US011918605B1

(12) United States Patent
Wagner et al.

(10) Patent No.: US 11,918,605 B1
(45) Date of Patent: Mar. 5, 2024

(54) CHIMERIC ANTIGEN RECEPTOR DENDRITIC CELL (CAR-DC) FOR TREATMENT OF CANCER

(71) Applicant: Myeloid Therapeutics, Inc., Cambridge, MA (US)

(72) Inventors: Samuel C. Wagner, San Diego, CA (US); Thomas E. Ichim, San Francisco, CA (US); Julia S. Szymanski, San Diego, CA (US); Santosh Kesari, San Diego, CA (US); Amit N. Patel, Salt Lake City, UT (US); Boris Minev, San Diego, CA (US)

(73) Assignee: MYELOID THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 17/975,187

(22) Filed: Oct. 27, 2022

Related U.S. Application Data

(63) Continuation of application No. 17/715,558, filed on Apr. 7, 2022, now Pat. No. 11,517,589, which is a continuation of application No. 17/559,967, filed on Dec. 22, 2021, which is a continuation of application No. 17/227,193, filed on Apr. 9, 2021, now abandoned, which is a continuation of application No. 15/048,922, filed on Feb. 19, 2016, now abandoned.

(60) Provisional application No. 62/118,027, filed on Feb. 19, 2015.

(51) Int. Cl.
*A61K 35/15* (2015.01)
*A61K 38/17* (2006.01)
*C07K 16/00* (2006.01)
*C07K 16/30* (2006.01)
*C07K 16/32* (2006.01)
*C12N 5/0786* (2010.01)

(52) U.S. Cl.
CPC ............ *A61K 35/15* (2013.01); *A61K 38/177* (2013.01); *C07K 16/00* (2013.01); *C07K 16/30* (2013.01); *C07K 16/32* (2013.01); *C12N 5/0645* (2013.01); *C07K 2317/622* (2013.01); *C07K 2319/03* (2013.01); *C07K 2319/33* (2013.01); *C12N 2501/599* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,225,539 A | 7/1993 | Winter | |
| 5,571,894 A | 11/1996 | Wels et al. | |
| 5,580,859 A | 12/1996 | Felgner et al. | |
| 5,585,089 A | 12/1996 | Queen et al. | |
| 5,587,458 A | 12/1996 | King et al. | |
| 5,591,828 A | 1/1997 | Bosslet et al. | |
| 5,633,234 A | 5/1997 | August et al. | |
| 5,639,642 A | 6/1997 | Kjeldsen et al. | |
| 5,641,870 A | 6/1997 | Rinderknecht et al. | |
| 5,693,761 A | 12/1997 | Queen et al. | |
| 5,766,903 A | 6/1998 | Sarnow et al. | |
| 5,773,244 A | 6/1998 | Ares, Jr. et al. | |
| 5,776,910 A | 7/1998 | Schreiber et al. | |
| 5,869,046 A | 2/1999 | Presta et al. | |
| 6,210,931 B1 | 4/2001 | Feldstein et al. | |
| 6,210,963 B1 | 4/2001 | Haddada et al. | |
| 6,248,516 B1 | 6/2001 | Winter et al. | |
| 6,455,299 B1 | 9/2002 | Steinman et al. | |
| 6,468,798 B1 | 10/2002 | Debs et al. | |
| 6,602,709 B1 | 8/2003 | Albert et al. | |
| 6,734,014 B1 | 5/2004 | Hwu et al. | |
| 6,936,468 B2 | 8/2005 | Robbins et al. | |
| 7,833,789 B2 | 11/2010 | Naldini et al. | |
| 7,926,300 B2 | 4/2011 | Roberts et al. | |
| 8,198,020 B2 | 6/2012 | Francois et al. | |
| 8,709,412 B2 | 4/2014 | Jones et al. | |
| 9,045,541 B2 | 6/2015 | Eckelman et al. | |
| 9,149,519 B2 | 10/2015 | Landau et al. | |
| 9,221,908 B2 | 12/2015 | Frazier et al. | |
| 9,428,569 B2 | 8/2016 | Spencer et al. | |
| 9,518,116 B2 | 12/2016 | Frazier et al. | |
| 9,663,575 B2 | 5/2017 | Eckelman et al. | |
| 9,745,368 B2 | 8/2017 | Milone et al. | |

(Continued)

FOREIGN PATENT DOCUMENTS

| | | |
|---|---|---|
| CA | 2850380 C | 8/2015 |
| EP | 0404097 A2 | 12/1990 |

(Continued)

OTHER PUBLICATIONS

Ali, M. et al., "Induction of neoantigen-reactive T cells from healthy donors", Nature Protocols (2019).

(Continued)

*Primary Examiner* — Daniel C Gamett
(74) *Attorney, Agent, or Firm* — Wilson Sonsini Goodrich & Rosati

(57) ABSTRACT

The current invention provides monocytic cells transfected with chimeric antigen receptor (CAR) to selectively home to tumors and upon homing differentiate into dendritic cells capable of activating immunity which is inhibitory to said tumor. In one embodiment of the invention, monocytic cells are transfected with a construct encoding an antigen binding domain, a transcellular or structural domain, and an intracellular signaling domain. In one specific aspect of the invention, the antigen binding domain interacts with sufficient affinity to a tumor antigen, capable of triggering said intracellular domain to induce an activation signal to induce monocyte differentiation into DC.

30 Claims, No Drawings

Specification includes a Sequence Listing.

(56) References Cited

U.S. PATENT DOCUMENTS

| | | |
|---|---|---|
| 9,820,350 B2 | 11/2017 | Pyshos et al. |
| 9,845,345 B2 | 12/2017 | Ring et al. |
| 9,850,312 B2 | 12/2017 | Agatsuma et al. |
| 9,913,920 B2 | 3/2018 | Movahedi et al. |
| 10,034,900 B2 | 7/2018 | Senju |
| 10,081,680 B2 | 9/2018 | Weiskopf et al. |
| 10,106,609 B2 | 10/2018 | Yang et al. |
| 10,155,038 B2 | 12/2018 | Rabinovich et al. |
| 10,259,859 B2 | 4/2019 | Pons et al. |
| 10,259,873 B2 | 4/2019 | Frazier et al. |
| 10,299,335 B2 | 5/2019 | Pyshos et al. |
| 10,415,017 B2 | 9/2019 | O'Neill |
| 10,428,143 B2 | 10/2019 | Krummel et al. |
| 10,602,584 B2 | 3/2020 | Pyshos et al. |
| 10,774,125 B2 | 9/2020 | Ring et al. |
| 10,980,836 B1 | 4/2021 | Getts et al. |
| 11,034,749 B2 | 6/2021 | Gill et al. |
| 11,517,589 B2 | 12/2022 | Wagner et al. |
| 2003/0130496 A1 | 7/2003 | Winter et al. |
| 2004/0053873 A1 | 3/2004 | Barman et al. |
| 2005/0031628 A1 | 2/2005 | George et al. |
| 2006/0018889 A1 | 1/2006 | Li et al. |
| 2006/188891 A1 | 8/2006 | Bickmore, Jr. et al. |
| 2008/0254027 A1 | 10/2008 | Bernett et al. |
| 2011/0250203 A1 | 10/2011 | Klitgaard et al. |
| 2011/0287038 A1 | 11/2011 | Slawin et al. |
| 2011/0293603 A1 | 12/2011 | Saraiva et al. |
| 2012/0045389 A1 | 2/2012 | Gassull Duro et al. |
| 2013/0280285 A1 | 10/2013 | Schonfeld et al. |
| 2014/0134142 A1 | 5/2014 | Smith et al. |
| 2014/0140989 A1 | 5/2014 | Eckelman et al. |
| 2014/0161805 A1 | 6/2014 | Jamieson et al. |
| 2014/0242701 A1 | 8/2014 | Shiku et al. |
| 2015/0057161 A1 | 2/2015 | Schultze et al. |
| 2015/0274826 A1 | 10/2015 | Frazier et al. |
| 2016/0045551 A1 | 2/2016 | Brentjens et al. |
| 2016/0137733 A1 | 5/2016 | Frazier et al. |
| 2016/0145348 A1 | 5/2016 | Stephan |
| 2016/0250258 A1 | 9/2016 | Delaney et al. |
| 2016/0251435 A1 | 9/2016 | Eckelman et al. |
| 2017/0087185 A1 | 3/2017 | Crane et al. |
| 2017/0151281 A1 | 6/2017 | Wagner et al. |
| 2017/0151282 A1 | 6/2017 | Discher et al. |
| 2017/0166657 A1 | 6/2017 | O'Neill et al. |
| 2017/0226183 A1 | 8/2017 | Schiffer-Mannioui |
| 2017/0233452 A1 | 8/2017 | McIvor et al. |
| 2017/0246278 A1 | 8/2017 | Vera Valdes et al. |
| 2017/0283498 A1 | 10/2017 | Frazier et al. |
| 2017/0292118 A1 | 10/2017 | Duchateau et al. |
| 2018/0000899 A1 | 1/2018 | Francois et al. |
| 2018/0030553 A1 | 2/2018 | Tang et al. |
| 2018/0057592 A1 | 3/2018 | Frazier et al. |
| 2018/0104308 A1 | 4/2018 | Mamonkin et al. |
| 2018/0105600 A1 | 4/2018 | Pons et al. |
| 2018/0133252 A9 | 5/2018 | Wilson et al. |
| 2018/0142019 A1 | 5/2018 | Manning et al. |
| 2018/0155405 A1 | 6/2018 | Ring et al. |
| 2018/0171021 A1 | 6/2018 | Karlsson et al. |
| 2018/0186878 A1 | 7/2018 | Rosenthal |
| 2018/0221503 A1 | 8/2018 | Kadiyala et al. |
| 2018/0244748 A1 | 8/2018 | Gill et al. |
| 2018/0250395 A1 | 9/2018 | Pietsch et al. |
| 2018/0319883 A1 | 11/2018 | Weiskopf et al. |
| 2018/0325953 A1 | 11/2018 | Poznansky et al. |
| 2018/0334653 A1 | 11/2018 | O'Neill |
| 2018/0355011 A1 | 12/2018 | Lim et al. |
| 2019/0008897 A1 | 1/2019 | Scatena et al. |
| 2019/0010219 A1 | 1/2019 | Short |
| 2019/0023761 A1 | 1/2019 | Pule et al. |
| 2019/0038671 A1 | 2/2019 | Fan et al. |
| 2019/0062450 A1 | 2/2019 | De Palma et al. |
| 2019/0070277 A1 | 3/2019 | O'Neill et al. |
| 2019/0112373 A1 | 4/2019 | Manning et al. |
| 2019/0119379 A1 | 4/2019 | Gottschalk et al. |
| 2019/0119396 A1 | 4/2019 | Liu et al. |
| 2019/0144522 A1 | 5/2019 | Bari et al. |
| 2019/0169266 A1 | 6/2019 | Pons et al. |
| 2019/0233496 A1 | 8/2019 | Rosenthal |
| 2019/0240343 A1 | 8/2019 | Ahmed et al. |
| 2019/0248892 A1 | 8/2019 | Frazier et al. |
| 2019/0263928 A1 | 8/2019 | Watanabe et al. |
| 2019/0275150 A1 | 9/2019 | Pincetic et al. |
| 2019/0336615 A1 | 11/2019 | Thompson et al. |
| 2019/0345217 A1 | 11/2019 | Ma et al. |
| 2019/0381158 A1 | 12/2019 | Gunn |
| 2020/0247870 A1 | 8/2020 | Gill et al. |
| 2020/0345773 A1 | 11/2020 | Getts et al. |
| 2020/0345774 A1 | 11/2020 | Getts et al. |
| 2021/0002377 A1 | 1/2021 | Brogdon et al. |
| 2021/0046110 A1 | 2/2021 | Gill et al. |
| 2021/0095001 A1 | 4/2021 | Gill et al. |
| 2021/0252053 A1 | 8/2021 | Wagner et al. |
| 2022/0000917 A1 | 1/2022 | Klichinsky et al. |
| 2022/0000918 A1 | 1/2022 | Klichinsky et al. |
| 2022/0002375 A1 | 1/2022 | Gill et al. |
| 2022/0002376 A1 | 1/2022 | Gill et al. |
| 2022/0002377 A1 | 1/2022 | Gill et al. |
| 2022/0002675 A1 | 1/2022 | Klichinsky et al. |
| 2022/0033465 A1 | 2/2022 | Gill et al. |
| 2022/0033466 A1 | 2/2022 | Gill et al. |
| 2022/0033467 A1 | 2/2022 | Gill et al. |
| 2022/0033468 A1 | 2/2022 | Gill et al. |
| 2022/0041688 A1 | 2/2022 | Gill et al. |
| 2022/0073639 A1 | 3/2022 | Ruella et al. |
| 2022/0098273 A1 | 3/2022 | Corey |
| 2022/0118010 A1 | 4/2022 | Wagner et al. |
| 2022/0175830 A1 | 6/2022 | Wagner et al. |
| 2022/0175831 A1 | 6/2022 | Wagner et al. |
| 2022/0202856 A1 | 6/2022 | Wagner et al. |
| 2022/0233586 A1 | 7/2022 | Wagner et al. |
| 2022/0241428 A1 | 8/2022 | Getts et al. |

FOREIGN PATENT DOCUMENTS

| | | |
|---|---|---|
| EP | 0338841 B1 | 3/1995 |
| EP | 2626415 A2 | 8/2013 |
| EP | 2953643 A1 | 12/2015 |
| EP | 2242512 B1 | 4/2016 |
| EP | 3197495 A1 | 8/2017 |
| EP | 3328402 A1 | 6/2018 |
| EP | 2956343 B1 | 12/2018 |
| EP | 3504244 A1 | 7/2019 |
| EP | 3519441 A1 | 8/2019 |
| EP | 3574018 A4 | 10/2020 |
| GB | 2572005 A | 9/2019 |
| WO | WO-9201813 A1 | 2/1992 |
| WO | WO-9301161 A1 | 1/1993 |
| WO | WO-9425591 A1 | 11/1994 |
| WO | WO-9505835 A1 | 3/1995 |
| WO | WO-1995005835 A1 | 3/1995 |
| WO | WO-02077029 A2 | 10/2002 |
| WO | WO-02077029 A3 | 5/2003 |
| WO | WO-2004050855 A2 | 6/2004 |
| WO | WO-2007113572 A1 | 10/2007 |
| WO | WO-2008011599 A2 | 1/2008 |
| WO | WO-2011028554 A1 | 3/2011 |
| WO | WO-2012005763 A1 | 1/2012 |
| WO | WO-2012045389 A1 | 4/2012 |
| WO | WO-2012170930 A1 | 12/2012 |
| WO | WO-2013123088 A1 | 8/2013 |
| WO | WO-2013185552 A1 | 12/2013 |
| WO | WO-2014055668 A1 | 4/2014 |
| WO | WO-2014123580 A1 | 8/2014 |
| WO | WO-2014153114 A1 | 9/2014 |
| WO | WO-2016033331 A1 | 3/2016 |
| WO | WO-2016040441 A1 | 3/2016 |
| WO | WO-2016070136 A1 | 5/2016 |
| WO | WO-2016126608 A1 | 8/2016 |
| WO | WO-2016149254 A1 | 9/2016 |
| WO | WO-2016172606 A1 | 10/2016 |
| WO | WO-2017025944 A2 | 2/2017 |
| WO | WO-2017044487 A1 | 3/2017 |
| WO | WO-2017050884 A1 | 3/2017 |
| WO | WO-2017025944 A3 | 4/2017 |

(56) References Cited

FOREIGN PATENT DOCUMENTS

| | | |
|---|---|---|
| WO | WO-2017136633 A1 | 8/2017 |
| WO | WO-2018038684 A1 | 3/2018 |
| WO | WO-2018064076 A1 | 4/2018 |
| WO | WO-2018140831 A3 | 8/2018 |
| WO | WO-2018169948 A1 | 9/2018 |
| WO | WO-2018231871 A1 | 12/2018 |
| WO | WO-2019005641 A1 | 1/2019 |
| WO | WO-2019032624 A1 | 2/2019 |
| WO | WO-2019067328 A1 | 4/2019 |
| WO | WO-2019070704 A1 | 4/2019 |
| WO | WO-2019086512 A1 | 5/2019 |
| WO | WO-2019129146 A1 | 7/2019 |
| WO | WO-2019191332 A1 | 10/2019 |
| WO | WO-2019191334 A1 | 10/2019 |
| WO | WO-2019191340 A1 | 10/2019 |
| WO | WO-2019201995 A1 | 10/2019 |
| WO | WO-2020095044 A1 | 5/2020 |
| WO | WO-2020097193 A1 | 5/2020 |
| WO | WO-2020223550 A1 | 11/2020 |
| WO | WO-2021263152 A1 | 12/2021 |
| WO | WO-2022036265 A1 | 2/2022 |
| WO | WO-2022067033 A1 | 3/2022 |

OTHER PUBLICATIONS

Alvey CM, Spinler KR, Irianto J, Pfeifer CR, Hayes B, Xia Y, Cho S, Dingal P, Hsu J, Smith L, Tewari M, Discher DE. 2017. SIRPA-Inhibited, Marrow-Derived macrophages engorge, accumulate, and differentiate in Antibody-Targeted regression of solid tumors. Current Biology 27:2065-2077.
Alvey et al. Engineering macrophages to eat Cancer: from "marker of self" CD47 and phagocytosis to differentiation. Journal of Leukocyte Biology 102:31-40 (2017).
Ancuta et al. (BMC Genomics 2009 10:403, pp. 1-19).
Andreesen R, Scheibenbogen C, Brugger W, Krause S, Meerpohl HG, Leser HG, Engler H, Lohr GW. 1990. Adoptive transfer of tumor cytotoxic macrophages generated in vitro from circulating blood monocytes: a new approach to Cancer immunotherapy. Cancer Research 50:7450-7456.
Andreu N, Phelan J, de Sessions PF, Cliff JM, Clark TG, Hibberd ML. 2017. Primary macrophages and J774 cells respond differently to infection with *Mycobacterium tuberculosis*. Scientific Reports 7:42225.
Application as filed for U.S. Appl. No. 17/202,018, filed Mar. 15, 2021.
Auffray et al. Blood monocytes: development, heterogeneity, and relationship with dendritic cells, Annual Rev. Immunol. 2009 27:669-92.
Batista FD, Iber D, Neuberger MS. 2001. B cells acquire antigen from target cells after synapse formation. Nature 411:489-494.
Beningo KA, Wang YL. 2002. Fc-receptor-mediated phagocytosis is regulated by mechanical properties of the target. Journal of Cell Science 115:849-856.
Berger, et al., Efficient Elutriation of monocytes within a closed system (Elutra™) Journal of Immunological Methods 298 (2005) 61-72.
Bhattacharjee, J., et al., "Monocytes isolated by positive and negative magnetic sorting techniques show different molecular characteristics and immunophenotypic behaviour", F100Research (2018) pp. 1-13.
Biglari, A., et al. Human monocytes expressing a CEA-specific chimeric CD64 receptor specifically target CEA-expressing tumour cells in vitro and in vivo, Gene Therapy (2006) 13, 602-610.
Blumenthal D. et al., (Nov. 10-14, 2021). "Development and Characterization of Chimeric Antigen Receptor Monocytes (CAR Mono), a Novel Cell Therapy Platform for Solid Tumor Immunotherapy." Poster Presentation. Society for Immunotherapy of Cancer (SITC) Meeting, Washington, DC, United States. https://secureservercdn.net/45.40.149.113/74d.fcf.myftpupload.com/wp-content/uploads/2021/11/Poster-104-Daniel-Blumenthal-Carisma-Therapeutics.pdf.
Blumenthal D. et al., (Apr. 8-13, 2022). "Pre-clinical development of CAR Monocytes (CAR Mono) for solid tumor immunotherapy." Poster Presentation. The American Association for Cancer Research (AACR) Annual Meeting, New Orleans, LA, United States. https://secureservercdn.net/45.40.149.113/74d.fcf.myftpupload.com/wp-content/uploads/2022/07/Poster-5000-Daniel-Blumenthal-Carisma-Therapeutics.pdf.
Bournazos, S., The Role and Function of Fcγ Receptors on Myeloid Cells Microbiol Spectr. Dec. 2016 ; 4(6):1-29.
Brooks SR, Kirkham PM, Freeberg L, Carter RH. 2004. Binding of cytoplasmic proteins to the CD19 intracellular domain is high affinity, competitive, and multimeric. The Journal of Immunology 172:7556-7564.
Bu JY, Shaw AS, Chan AC. 1995. Analysis of the interaction of ZAP-70 and syk protein-tyrosine kinases with the T-cell antigen receptor by plasmon resonance. PNAS 92:5106-5110.
"Burgueno-Bucio et al. "The multiple faces of CD5" J. Leukoc Bio. (2019) 105:891-904".
Calderwood, David, "Integrin Activation" Journal of Cell Science (2004) 117, pp. 657-666.
Carisma Therapeutics. "Carisma Therapeutics Corporate Overview." Nov. 2018.
Chao MP, Alizadeh AA, Tang C, Myklebust JH, Varghese B, Gill S, Jan M, Cha AC, Chan CK, Tan BT, Park CY, Zhao F, Kohrt HE, Malumbres R, Briones J, Gascoyne RD, Lossos IS, Levy R, Weissman IL, Majeti R. 2010. Anti-CD47 antibody synergizes with rituximab to promote phagocytosis and eradicate non-Hodgkin lymphoma. Cell 142:699-713.
Chen J, Zhong MC, Guo H, Davidson D, Mishel S, Lu Y, Rhee I, Pe' rez-Quintero LA, Zhang S, Cruz-Munoz ME, Wu N, Vinh DC, Sinha M, Calderon V, Lowell CA, Danska JS, Veillette A. 2017. SLAMF7 is critical for phagocytosis of haematopoietic tumour cells via Mac-1 integrin. Nature 544:493-497.
Corresponding PCT Application No. PCT/US2019/060052, filed Nov. 6, 2019.
Cros, et al., "Human CD14dim) Monocytes Patrol and Sense Nucleic Acids and viruses via TLR7 and TLR8 Receptors", Immunity 33, 375-386, Sep. 24, 2010.
Cross SE, Jin YS, Rao J, Gimzewski JK. 2007. Nanomechanical analysis of cells from cancer patients. Nature Nanotechnology 2:780-783.
Daeron et al. Fc Receptors. Current Topics in Microbiology and Immunology, vol. 382. 2014.
Davis SJ, van der Merwe PA. 2006. The kinetic-segregation model: TCR triggering and beyond. Nature Immunology 7:803-809.
De Oliveria, S, et al., "Modification of Hematopoietic Stem/Progenitor Cells with CD19-Specific Chimeric Antigen Receptros as a Novel Approach for Cancer Immunotherapy" Human Gene Therapy 24:824-839 (Oct. 2013).
Dotti et al. Design and Development of Therapies using Chimeric Antigen Receptor-Expressing T cells. Immunol Rev. 257(1):35 pgs (2014).
Edelstein A, Amodaj N, Hoover K, Vale R, Stuurman N. 2010. Computer control of microscopes using manager. Current Protocols in Molecular Biology 14:Unit14.20.
Engel P, Zhou LJ, Ord DC, Sato S, Koller B, Tedder TF. 1995. Abnormal B lymphocyte development, activation, and differentiation in mice that lack or overexpress the CD19 signal transduction molecule. Immunity 3:39-50.
Fesnak AD, June CH, Levine BL. 2016. Engineered T cells: the promise and challenges of cancer immunotherapy. Nature Reviews Cancer 16:566-581.
Fraser, A., et al., "Development, functional characterization and validation of methodology for GMP-compliant manufacture of phagocytic macrophages: A novel cellular therapeutic for liver cirrhosis", Cyotherapy, 2017, ISSN 1465-3249.
Freeman SA, Goyette J, Furuya W, Woods EC, Bertozzi CR, Bergmeier W, Hinz B, van der Merwe PA, Das R, Grinstein S. 2016. Integrins Form an Expanding Diffusional Barrier that Coordinates Phagocytosis. Cell 164: 128-140.

(56) References Cited

OTHER PUBLICATIONS

Freeman SA, Grinstein S. 2014. Phagocytosis: receptors, signal integration, and the cytoskeleton. Immunological Reviews 262:193-215.
Gabitova L. et al., (Apr. 10-15, 2021 and May 17-21). "Anti-HER2 CAR monocytes demonstrate targeted anti-tumor activity and enable a single day cell manufacturing process." Poster Presentation. The American Association for Cancer Research (AACR) Annual Meeting, Philadelphia, PA, United States. https://secureservercdn.net/45.40.149.113/74d.fcf.myftpupload.com/wp-content/uploads/2021/09/Anti-HER2-CAR-monocytes_AACR2021.pdf.
Gardai SJ, McPhillips KA, Frasch SC, Janssen WJ, Starefeldt A, Murphy-Ullrich JE, Bratton DL, Oldenborg PA, Michalak M, Henson PM. 2005. Cell-surface calreticulin initiates clearance of viable or apoptotic cells through trans-activation of LRP on the phagocyte. Cell 123:321-334.
"Geissmann, et al., "Blood Monocytes Consist of Two Principal Subsets with Distinct Migratory Properties", Immunity, vol. 19, pp. 71-82, Jul. 2003".
"Getts, et al., "Microparticles bearing encephalitogenic peptides induce T-cell tolerance and ameliorate experimental autoimmune encephalomyelitis" (2012) Nat Biotechnol. 30(12) pp. 1217-1224".
Gordon, S., Phagocytosis an immunobiologic process. Immunity 44, Mar. 15, 2016 p. 463-475.
Goudot, C. et al., "Aryl Hydrocarbon Receptro Controls Monocyte Differentiation into Dendritic Cells versus Macrophages", Sep. 19, 2017 Immunity 47, 582-596.
"Harburger, et al., "Integrin signalling at a glance" (2009) Journal of Cell Sciences 122".
Harshyne LA, Zimmer MI, Watkins SC, Barratt-Boyes SM. 2003. A Role for Class A Scavenger Receptor in Dendritic Cell Nibbling from Live Cells. The Journal of Immunology 170:2302-2309.
Harshyne LA, Watkins SC, Gambotto A, Barratt-Boyes SM. 2001. Dendritic cells acquire antigens from live cells for Cross-Presentation to CTL. The Journal of Immunology 166:3717-3723.
Haso W, Lee DW, Shah NN, Stetler-Stevenson M, Yuan CM, Pastan IH, Dimitrov DS, Morgan RA, FitzGerald DJ, Barrett DM, Wayne AS, Mackall CL, Orentas RJ. 2013. Anti-CD22-chimeric antigen receptors targeting B-cell precursor acute lymphoblastic leukemia. Blood 121:1165-1174.
Huang, Min-Nung, et al., "Antigen-loaded monocyte administration induces potent therapeutic antitumor T cell responses", The Journal of Clinical Investigation, Jan. 6, 2020, pp. 1-15.
Hui E, Vale RD. 2014. In vitro membrane reconstitution of the T-cell receptor proximal signaling network. Nature Structural & Molecular Biology 21:133-142.
Hui, et al., "T cell constimulatory receptor CD28 is a primary target for PD-1-mediated inhibition" (2017) Science 355(6332) p. 1428-1433.
"Silverstein, et al., "Mechanisms of Cell Signaling by the Scavenger Receptor CD36: Implications in Atherosclerosis and Thrombosis" Transactions of the American Clinical and Climatological Association, vol. 121 (2010), vol. 121".
Ingersoll, Ph.D., Brooke, "Brief Report: Pilot Randomized Controlled Trial of Reciprocal Imitation Training for Teaching Elicited and Spontaneous Imitation to Children with Autism", J Autism Dev Disord. Sep. 2010; 40(9): 1154-1160.
International Search Report and Written Opinion for corresponding PCT/US2020/030837 dated Oct. 1, 2020.
Italiani P, Boraschi D. "From Monocytes to M1/M2 Macrophages: Phenotypical vs. Functional Differentiation." Front Immunol. Oct. 17, 2014;5:514.
Jadus MR, Irwin MC, Irwin MR, Horansky RD, Sekhon S, Pepper KA, Kohn DB, Wepsic HT. 1996. Macrophages can recognize and kill tumor cells bearing the membrane isoform of macrophage colony-stimulating factor. Blood 87:5232-5241.
Jaiswal S, Jamieson CH, Pang WW, Park CY, Chao MP, Majeti R, Traver D, van Rooijen N, Weissman IL. 2009. CD47 is upregulated on circulating hematopoietic stem cells and leukemia cells to avoid phagocytosis. Cell 138:271-285.
James JR, Vale RD. 2012. Biophysical mechanism of T-cell receptor triggering in a reconstituted system. Nature 487:64-69.
Jarrsson-Wuilleme et al.: Transduction of nondividing human macrophages with gammaretrovirus-derived vectors. J Virol. 80(3):1152-1159 doi:10.1128/JVI.80.3.1152-1159.2006 (2006).
Joly E, Hudrisier D. 2003. What is trogocytosis and what is its purpose? Nature Immunology 4:815.
Kao G, Huang CC, Hedgecock EM, Hall DH, Wadsworth WG. 2006. The role of the laminin beta subunit in laminin heterotrimer assembly and basement membrane function and development in C. elegans. Developmental Biology 290:211-219.
Kim, et al., "Monocyte Enrichment from Leukapheresis products by using the Elutra cell separator" Transfusion, vol. 47, Dec. 2007 pp. 2290-2296.
Klichinsky M. et al., "CAR-Macrophage for Cancer Immunotherapy: Latest Findings from the CT-0508 Clinical Trial" YouTube, https://youtu.be/2Ag7SVM-fPg, published Jun. 27, 2022, https://carismatx.com/programs/ct-0508/.
Klichinsky M et al., "Human chimeric antigen receptor macrophages for cancer immunotherapy." Nat Biotechnol. Aug. 2020;38(8):947-953. Epub Mar. 23, 2020.
Kochenderfer JN, Feldman SA, Zhao Y, Xu H, Black MA, Morgan RA, Wilson WH, Rosenberg SA. 2009. Construction and preclinical evaluation of an anti-CD19 chimeric antigen receptor. Journal of Immunotherapy 32:689-702.
Lacerna LV, Stevenson GW, Stevenson HC. 1988. Adoptive cancer immunotherapy utilizing lymphokine activated killer cells and gamma interferon activated killer monocytes. Pharmacology & Therapeutics 38:453-465.
"Laird et al. (J. Leukocyte Biology 2009, 85: 966-977)".
Lee S, Kivimae S, Dolor A, Szoka FC. 2016. Macrophage-based cell therapies: the long and winding road. Journal of Controlled Release 240:527-540.
Lim WA, June CH, Huang J, Hodes RJ. 2017. The Principles of Engineering Immune Cells to Treat Cancer. Cell 168:724-740.
Liu X, Pu Y, Cron K, Deng L, Kline J, Frazier WA, Xu H, Peng H, Fu YX, Xu MM. 2015. CD47 blockade triggers T cell-mediated destruction of immunogenic tumors. Nature Medicine 21:1209-1215.
Lloyd et al. Modelling the human immune response: performance of a 1011 human antibody repertoire against a broad panel of therapeutically relevant antigens. Protein Eng Des Sel 22(3):159-168 (2009).
Majeti R, Chao MP, Alizadeh AA, Pang WW, Jaiswal S, Gibbs KD, van Rooijen N, Weissman IL. 2009. CD47 is an adverse prognostic factor and therapeutic antibody target on human acute myeloid leukemia stem cells. Cell 138:286-299.
"Matsuyoshi, Hidetake, et al., "Enchanced Priming of Antigen-Specific CTL's In Vivo by Embryonic Stem Cell-Derived Dendritic Cells Expressing Chemokine Along with Antigenic Protein: Application to Antitumor Vaccination", The Journal of Immunology (2004) 172:776-786".
Mayordomo JI, Zorina T, Storkus WJ, Zitvogel L, Celluzzi C, Falo LD, Melief CJ, Ildstad ST, Kast WM, Deleo AB. 1995. Bone marrow-derived dendritic cells pulsed with synthetic tumour peptides elicit protective and therapeutic antitumour immunity. Nature Medicine 1:1297-1302.
"McEver, et al., "Selectins: initiators of leucocyte adhesion and signalling at the vascular wall" Cardovascular Research (2015) 107, pp. 331-339".
"Mildner, A., et al., "Distinct and Non-Redundant Roles of Microglia and Myeloid Subsets in Mouse Models of Alzheimer's Disease" Neurobiology of Disease, J. Neurosci., Aug. 3, 2011, 31(31):11159-11171".
Morrissey, M., et al., "Chimeric antigen receptros that trigger phagocytosis", eLife 2018, pp. 1/21.
Mukherjee, R. et al., "Non-Classical monocytes display inflammatory features: Validation in Sepsis and Systemic Lupus Erythematous", Scientific Reports, (2015) pp. 1-14.
Murshid, et al., "Hsp90-peptide complexes stimulate antigen presentation through the class II pathway after binding scavenger receptor SREC-I" Immunobiology (2014) 219(12) pp. 924-931.
"Soderberg et al. (J. Virology 1993 67(6): 3166-3175)".

(56) References Cited

OTHER PUBLICATIONS

Olingy CE et al., "Monocyte heterogeneity and functions in cancer." J Leukoc Biol. Aug. 2019;106(2):309-322. doi: 10.1002/JLB. 4RI0818-311R. Epub Feb. 18, 2019.

Orecchioni M et al., "Macrophage Polarization: Different Gene Signatures in M1(LPS+) vs. Classically and M2(LPS−) vs. Alternatively Activated Macrophages." Front Immunol. May 24, 2019;10:1084. Erratum in: Front Immunol. Feb. 25, 2020;11:234.

Oshi M, et al., "M1 Macrophage and M1/M2 ratio defined by transcriptomic signatures resemble only part of their conventional clinical characteristics in breast cancer." Sci Rep. Oct. 6, 2020;10(1):16554.

"Oviedo-Boyso, et al., "The Phosphoinositide-3-Kinase-Akt Signaling Pathway Is Important for *Staphylococcus aureus* Internalization by Endothelial Cells" (2011) Infection and Immunity, vol. 79, No. 11, p. 4569-4577".

Oviedo-Boyso J., The Phosphoinositide-3-Kinase-Akt Signaling Pathway Is Important for *Staphylococcus aureus* Internalization by Endothelial Cells, Infection and Immunity, Nov. 2011, p. 4569-4577.

Passlick, et al., "Identification and Characterization of a Novel Monocyte Subpopulation in Human Peripheral Blood", Article in Blood, Dec. 1989, 74: 2527-2534.

PCT/US2019/060052 International Search Report and Written Opinion dated Apr. 30, 2020.

PCT/US2020/037312 International Search Report dated Nov. 30, 2020.

PCT/US2020/049240 International Search Report dated Mar. 26, 2021.

PCT/US2020/064686 International Search Report and Written Opinion dated Apr. 6, 2021.

Penberthy KK, Ravichandran KS. 2016. Apoptotic cell recognition receptors and scavenger receptors. Immunological Reviews 269:44-59.

Pierini S. et al., (Nov. 9-14, 2020). "Chimeric antigen receptor macrophages (CAR-M) elicit a systemic anti-tumor immune response and synergize with PD-1 blockade in immunocompetent mouse models of HER2+ solid tumors." Poster Presentation. Society for Immunotherapy of Cancer (SITC) Meeting, Virtual. https://secureservercdn.net/45.40.149.113/74d.fcf.myftpupload.com/wp-content/uploads/2021/09/CAR-M-syngeneic-model_SITC2020.pdf.

Pierini S. et al., (Apr. 8-13, 2022). "Chimeric antigen receptor macrophages (CAR-M) sensitize solid tumors to anti-PD1 immunotherapy." Poster Presentation. The American Association for Cancer Research (AACR) Annual Meeting, New Orleans, LA, United States. https://secureservercdn.net/45.40.149.113/74d.fcf.myftpupload.com/wp-content/uploads/2022/07/AACR2022_CARMaPD11.pdf.

Ralston KS, Solga MD, Mackey-Lawrence NM, Somlata , Bhattacharya A, Petri WA. 2014. Trogocytosis by Entamoeba histolytica contributes to cell killing and tissue invasion. Nature 508:526-530.

Reiss K. et al., (Nov. 10-14, 2021). "LBA (951): A Phase 1 first in human study of adenovirally transduced anti-HER2 CAR Macrophages in subjects with HER2 overexpressing solid tumors: preliminary safety, pharmacokinetics, and TME reprogramming data." Poster Presentation. Society for Immunotherapy of Cancer (SITC) Meeting, Washington, DC, United States. https://secureservercdn.net/45.40.149.113/74d.fcf.myftpupload.com/wp-content/uploads/2021/11/Poster-LBA951-CT-0508-Study-101-SITC-FINAL.pdf.

Reiss K. et al., (Jun. 3-7, 2022). "A Phase 1, First-In-Human (FIH) Study of the Anti-HER2 CAR Macrophage CT-0508 in Participants with HER2 Overexpressing Solid Tumors." Poster Presentation. American Society of Clinical Oncology (ASCO) Annual Meeting, New Chicago, IL, United States. https://secureservercdn.net/45.40.149.113/74d.fcf.myftpupload.com/wp-content/uploads/2022/07/ASCO-Data-In-Person-2022.final_.pdf.

Roberts EW, Broz ML, Binnewies M, Headley MB, Nelson AE, Wolf DM, Kaisho T, Bogunovic D, Bhardwaj N, Krummel MF. 2016. Critical Role for CD103(+)/CD141(+) Dendritic Cells Bearing CCR7 for Tumor Antigen Trafficking and Priming of T Cell Immunity in Melanoma. Cancer Cell 30:324-336.

Roberts, Margo R., et al., "Antigen-Specific Cytolysis by Neutrophils and NK Cells Expressing Chimeric Immune Receptros Bearing xx Signaling Domains", J Immunol 1998; 161:375-384.

Rosales, C. et al., "Phagocytosis: A Fundamental Process in Immunity", BioMed Research International, vol. 2017, Article ID 9042851, 18 pages.

Ruiz-Aguilar, S., et al., "Human CD16+ and CD16+ monocyte subsets display unique effector properties in inflammatory conditions in vivo", Journal of Leukocyte Biology, (2011) vol. 90, pp. 1119-1131.

Schlam D, Bagshaw RD, Freeman SA, Collins RF, Pawson T, Fairn GD, Grinstein S. 2015. Phosphoinositide 3-kinase enables phagocytosis of large particles by terminating actin assembly through Rac/Cdc42 GTPase-activating proteins. Nature Communications 6:8623.

Schlam, et al., "Phosphoinositide 3-kinase enables phagocytosis of large particles by terminating actin assembly through Rac/Cdc42 GRPase-activating proteins" (2015) Nature Communications.

Senju, et al., "Generation of dendritic cells and macrophages from human induced pluripotent stem cells aiming at cell therapy" Gene Therapy (2011) 18, 874-883.

Senju, Satoru, et al., "Generation and genetic modification of dendritic cells derived from mouse embryonic stem cells derived from mouse embryonics stem cells", Blood, May 1, 2003, vol. 101, No. 9, pp. 3501-3508.

Sloas C. et al., (Nov. 10-14, 2021). "SIRPα-Deficient CAR-Macrophages Exhibit Enhanced Anti-Tumor Function and Bypass the CD47 Immune Checkpoint." Poster Presentation. Society for Immunotherapy of Cancer (SITC) Meeting, Washington, DC, United States. https://secureservercdn.net/45.40.149.113/74d.fcf.myftpupload.com/wp-content/uploads/2021/11/CRISPR_CAR-M_Poster_101721_share-Read-Only.pdf.

Su X, et al., Phase separation of signaling molecules promotes T cell receptor signal transduction, Science. Apr. 29, 2016; 352(6285): 595-599.

"Tippet et al. (J. Leukocyte Biology 2013 93: 913-920)".

"Strauss, et al., "The immunophenotype of antigen presenting cells of the mononuclear phagocyte system in a normal human liver—A systematic review" Journal of Hepatology, (2015) vol. 62, pp. 458-468".

Tseng D, Volkmer JP, Willingham SB, Contreras-Trujillo H, Fathman JW, Fernhoff NB, Seita J, Inlay MA, Weiskopf K, Miyanishi M, Weissman IL. 2013. Anti-CD47 antibody-mediated phagocytosis of cancer by macrophages primes an effective antitumor T-cell response. PNAS 110:11103-11108.

Tsutsui, et al. "The use of microbubbles to target drug delivery" Cardiovascular Ultrasound (2004) 2:23.

Tuveson DA, Carter RH, Soltoff SP, Fearon DT. 1993. CD19 of B cells as a surrogate kinase insert region to bindphosphatidylinositol 3-kinase. Science 260:986-989.

Weischenfeldt J, Porse B. 2008. Bone Marrow-Derived Macrophages (BMM): Isolation and Applications. Cold Spring Harbor Protocols 2008:pdb.prot5080.

"Wilkinson et al. (Med. Microbio. Immunol. 2015 204:273-284)".

Wong KL et al., "The three human monocyte subsets: implications for health and disease." Immunol Res. Sep. 2012;53(1-3):41-57. Epub Mar. 20, 2012.

Xiao X, Ho M, Zhu Z, Pastan I, Dimitrov DS. 2009. Identification and characterization of fully human anti-CD22 monoclonal antibodies. mAbs 1:297-303.

Yong, C., et al., "A role for multiple chimeric antigen receptor-expressing leukocytes in antigen-specific responses to cancer" (2016) Oncotarget, vol. 7, No. 23 pp. 34582-34598.

Altschul et al., Basic local alignment search tool. J. Mol. Biol. 215:403-410 (1990).

Benton et al.: Screening lambdagt recombinant clones by hybridization to single plaques in situ. Science. 196(4286):80-182 (1977).

Devereux et al., A comprehensive set of sequence analysis programs for the VAX. Nucleic Acids Res. Jan. 11, 1984;12(1 Pt 1):387-95.

Final Office Action issued in corresponding U.S. Appl. No. 17/715,710 dated Apr. 6, 2023.

(56) References Cited

OTHER PUBLICATIONS

Final Office Action issued in corresponding U.S. Appl. No. 17/227,193 dated Mar. 8, 2022.
Final Office Action issued in corresponding U.S. Appl. No. 15/048,922 dated Jul. 13, 2018.
Getts et al.: Harnessing nanoparticles for immune modulation. Trends Immunol 36(7):419-427 (2015).
Grunstein et al.: Colony hybridization: a method for the isolation of cloned DNAs that contain a specific gene. Proc Natl Acad Sci 72, (10):3961-3965 (1975).
Guatelli et al.: Isothermal, in vitro amplification of nucleic acids by a multienzyme reaction modeled after retroviral replication. Proc Natl Acad. Sci. 87(5)1874-1878 (1990).
Harland et al.: Stability of RNA in developing Xenopus embryos and identification of a destabilizing sequence in TFIIIA messenger RNA. Development 102(4):837-852 (1988).
Hollinger P. et al.: Diabodies: small bivalent and bispecific antibody fragments. Proc Natl Acad Sci 90(14):6444-6448 (1993).
Hsu et al.: Electron microscopic evidence for the circular form of RNA in the cytoplasm of eukaryotic cells. Nature 280:339-340 (1979).
Hudson et al.: Engineered antibodies. Nature Medicine 9(1):129-134 (2003).
Jeck et al.: Circular RNAs are abundant, conserved, and associated with ALU repeats. RNA 19:41-157 (2013).
Kievits et al.: NASBATM isothermal enzymatic in vitro nucleic acid amplification optimized for the diagnosis of HIV-1 infection. J. Virol. Methods 35:273-286 (1991).
Kimmel et al.: Preparation of cDNA and the generation of cDNA libraries: overview. Methods Enzymol 152:307-316 (1987).
Kwoh et al.: Transcription-based amplification system and detection of amplified human immunodeficiency virus type 1 with a bead-based sandwich hybridization format. Proc Natl Acad Sci 86(4):1173-1177 (1989).
Levine et al.: Global Manufacturing of CAR T Cell Therapy. Mol Ther Methods Clin Dev. 4:92-101 (2016).
McCaffrey et al.: RNA Interference in Adult Mice. Nature 418:38-39 (2002).
Medzihradszky, K.F.: Lessons in de novo peptide sequencing by tandem mass spectrometry. Mass Spectrom Rev 34(1):43-63 (2015).
Memczak et al.: Circular RNAs are a large class of animal RNAs with regulatory potency. Nature 495:333-338 (2013).

Nakamizo et al.: Single-cell analysis of human skin identifies CD14+ type 3 dendritic cells co-producing IL1B and IL23A in psoriasis. J Exp Med 218(9):e20202345 (2021). https://doi.org/10.1084/jem.20202345.
Oates et al.: Characterizing the polarization continuum of macrophage subtypes M1, M2a and M2c. bioRxiv (2022). doi: https://doi.org/10.1101/2022.06.13.495868.
Office Action issued in corresponding U.S. Appl. No. 17/715,710 dated Nov. 30, 2022.
Office Action issued in U.S. Appl. No. 17/227,193 dated Jun. 22, 2022.
Office Action issued in corresponding U.S. Appl. No. 17/227,193 dated Nov. 12, 2021.
Office Action issued in corresponding U.S. Appl. No. 15/048,922 dated Sep. 21, 2017.
Office Action issued in corresponding U.S. Appl. No. 15/048,922 dated Oct. 7, 2019.
Pluckthun et al.: The Pharmacology of Monoclonal Antibodies. Springer-Verlag 11:69-315 (1994).
Putnam. Antisense strategies and therapeutic applications. Am. J. Health Syst. Pharm. 53:151-160 (1996), erratum at Am. J. Health Syst. Pharm. 53:325 (1996).
Russell, D.G.: *Mycobacterium tuberculosis* and the intimate discourse of a chronic infection. Immunol Rev 240(1):252-268 (2011).
Scherberich et al.: CD14++ monocytes, CD14+/CD16+ subset and soluble CD14 as biological markers of inflammatory systemic diseases and monitoring immunosuppressive therapy. Clin Chem Lab Med. 37(3):209-13 (1999).
Schroers R, et al. Transduction of human PBMC-derived dendritic cells and macrophages by an HIV-1-based lentiviral vector system. Mol Ther. Feb. 2000;1(2):171-9.
Villanueva MT. Macrophages get a CAR. Nat Rev Drug Discov. 19(5):308 (2020).
Wahl et al.: Molecular hybridization of immobilized nucleic acids: theoretical concepts and practical considerations. Methods Enzymol 152:399-407 (1987).
Walker et al.: Strand displacement amplification—an isothermal, in vitro DNA amplification technique. Nucleic Acids Res 20(7):1691-1696 (1992).
Xia et al.: siRNA-mediated gene silencing in vitro and in vivo. Nat Biotechnol. 20:1006-1010 (2002).
Xiao et al.: Electrophysiological Characteristics of Primary Afferent Fibers After Systemic Administration of Anti-GC2 Ganglioside Antibody, Pain69: 145-151 (1997).
Yong et al.: Using electroporation to determine function of a chimeric antigen receptor in T cell and macrophage cell lines. The Open Gene Therapy Journal 23:5(1) (2013).

CHIMERIC ANTIGEN RECEPTOR DENDRITIC CELL (CAR-DC) FOR TREATMENT OF CANCER

CROSS-REFERENCE TO RELATED APPLICATION

This application claims the benefit of U.S. Provisional Application No. 62/118,027 filed on Feb. 19, 2015, the contents of which are incorporated herein by reference in its entirety.

SEQUENCE LISTING

The instant application contains a Sequence Listing which has been submitted electronically in XML format and is hereby incorporated by reference in its entirety. Said XML copy, created on Dec. 20, 2022, is named 56371-720_308_SL.xml and is 57,309 bytes in size.

FIELD OF THE INVENTION

The present disclosure generally relates to the fields of genetics, immunology and medicine. The invention pertains to the field of immunotherapy, more specifically the invention pertains to the utilization of monocytes that have been manipulated to home to tumor cells and upon binding to tumor antigens differentiating into monocytes with cytotoxic properties to tumors, or dendritic cells.

BACKGROUND OF THE INVENTION

The immune system possesses the power to cure cancers based on published reports of immunologically mediated spontaneous regressions, which have been document in colon, lung, melanoma, liver, breast. Intriguingly, spontaneous regression clinically, as well as in an animal model of spontaneous regression, seems to be associated primarily with stimulation of the innate immune system, comprising of macrophages, NK cells, NKT cells and neutrophils. Despite the original promising of immunotherapy, which will be mentioned, the field has focused on the adaptive immune response, specifically stimulation of T and B cells, and only recently has interest re-ignited in the innate immune system.

The use of the immune system to treat cancer is theoretically appealing due to the possibility of low toxicity, immunological memory, and ability to attack metastatic disease. Early studies suggested that vaccination to tumor antigens and tumors themselves may be possible. Specifically, Prehn back in 1957, obtained murine tumors and exposed them to irradiation to increase immunogenicity. When these tumors were implanted into animals they were rejected. Subsequent administration of the original tumors resulted in rejection of the tumors, thus suggesting that tumor specific antigens exist, which can stimulate immunity, especially subsequent to addition of a cellular stress such as irradiation. Twenty years later, using the same system it was demonstrated that cytotoxic T cells infiltrated the tumors that were implanted after rejection of the radiation induced tumors, thus demonstrating conclusively that rejection was immunologically mediated, despite the fact that the tumors were syngeneic. In humans, one of the original observations of immunological response to neoplasia was in patients with paraneoplastic disease in which immune response to breast cancer antigens results in a multiple sclerosis-like disease caused by cross reactive immunity to neural antigens that are found on the breast cancer. Specific identification of tumor antigens on a molecular basis led to the discovery that some of the antigens are either self-proteins aberrantly expressed, or mutations of self proteins.

Originally observations were made in patients bearing metastatic melanomas, and then subsequently in other tumors, that the tumors are infiltrated with various immunological components. These tumor infiltrating lymphocytes (TILs), contain populations of cells and individual clones that demonstrate tumor specificity; they lyse autologous tumor cells but not natural killer targets, allogeneic tumor cells, or autologous fibroblasts.

By isolating and expanding TILs in vitro, and then molecularly identifying what they are responding to, a variety of the well-known tumor agents have been discovered such as MAGE-1, and MAGE-3, GAGE-1, MART-1, Melan-A, gp100, gp75 (TRP-2), tyrosinase, NY-ESO-1, mutated p16, and beta catenin. It is interesting that in the case of some antigens, such as gp75, the peptide that elicits tumor rejection results from translation of an alternative open reading frame of the same gene. Thus, the gp75 gene encodes two completely different polypeptides, gp75 as an antigen recognized by immunoglobulin G antibodies in sera from a patient with cancer, and a 24-amino acid product as a tumor rejection antigen recognized by T cells. Peptides used for immunization generally are 8-9 amino acids which have been demonstrated to be displayed in association with class I MHC molecules for recognition by T cells, and tumor cells have been shown to express these naturally processed epitopes.

Despite the intellectual appeal of peptide based cancer vaccines, the response rate has been disappointingly low. According to a review by Steven Rosenberg's group at the NIH, the rate of objective response out of 440 patients treated at his institute was a dismal 2.6%.

The ability to make a universal yet versatile system to generate T cells that are capable of recognizing various types of cancers has important clinical implications for the use of T cell-based therapies, this concept was approach initially by Rosenberg's group in the ex vivo expansion of tumor infiltrating lymphocytes. One current strategy incorporates the use of genetic engineering to express a chimeric antigen receptor (CAR) on T cells. The extracellular domain of a typical CAR consists of the $V_H$ and \i$_L$ domains—single-chain fragment variable (scFv)—from the antigen binding sites of a monoclonal antibody. The scFv is linked to a flexible transmembrane domain followed by a tyrosine-based activation motif such as that from CDK The so-called second and third generation CARs include additional activation domains from co-stimulatory molecules such as CD28 and CD137 (41BB) which serve to enhance T cell survival and proliferation. CAR T cells offer the opportunity to seek out and destroy cancer cells by recognizing tumor-associated antigens (TAA) expressed on their surface. As such, the recognition of a tumor cells occurs via an MHC-independent mechanism.

Various preclinical and early-phase clinical trials highlight the efficacy of CAR T cells to treat cancer patients with solid tumors and hematopoietic malignancies. Despite of the promise that CAR T cells might have in treating cancer patients there are several limitations to the generalized clinical application of CAR T cells. First, since no single tumor antigen is universally expressed by all cancer types, scFv in CAR needs to be constructed for each tumor antigen to be targeted. Second, the financial cost and labor-intensive tasks associated with identifying and engineering scFvs against a variety of tumor antigens poses a major challenge.

Third, tumor antigens targeted by CAR could be downregulated or mutated in response to treatment resulting in tumor evasion. Since current CAR T cells recognize only one target antigen, such changes in tumors negate the therapeutic effects. Therefore, the generation of CAR T cells capable of recognizing multiple tumor antigens is highly desired. Finally, CAR T cells react with target antigen weakly expressed on non-tumor cells, potentially causing severe adverse effects. To avoid such "on-target off-tumor" reaction, use of scFvs with higher specificity to tumor antigen is required. And although ongoing studies are focused on generating methods to shut off CAR T cells in vivo this system has yet to be developed and might pose additional inherent challenges.

The current patent seeks to apply chimeric antigen receptor technology to activation of monocytes, which naturally home into tumors, to differentiated intratumorally said monocytes into dendritic cells which are capable of antigen presentation, as well as direct killing of tumors.

DETAILED DESCRIPTION OF THE INVENTION

Chimeric antigen receptor (CAR) cellular therapeutics have revolutionized the treatment of B cell malignancies achieving stunning success rates. Unfortunately, solid tumors have yet to benefit from this treatment. Additionally, patients treated with CAR-T cells lack B cells for the rest of their lives, as well as having the possibility of tumor lysis syndrome. This is in part due to the permanence of the CAR-T cells in the patients after treatment. The current invention applies the use of CAR technology to monocytes with the purpose of inducing differentiation to dendritic cells (DC) subsequent to contact with tumor antigens. Given that monocytes have a fixed mitotic index, fears of permanent manipulation of the host are diminished.

"Treating a cancer", "inhibiting cancer", "reducing cancer growth" refers to inhibiting or preventing oncogenic activity of cancer cells. Oncogenic activity can comprise inhibiting migration, invasion, drug resistance, cell survival, anchorage-independent growth, non-responsiveness to cell death signals, angiogenesis, or combinations thereof of the cancer cells.

The terms "cancer", "cancer cell", "tumor", and "tumor cell" are used interchangeably herein and refer generally to a group of diseases characterized by uncontrolled, abnormal growth of cells (e.g., a neoplasia). In some forms of cancer, the cancer cells can spread locally or through the bloodstream and lymphatic system to other parts of the body ("metastatic cancer").

"Ex vivo activated lymphocytes", "lymphocytes with enhanced antitumor activity" and "dendritic cell cytokine induced killers" are terms used interchangeably to refer to composition of cells that have been activated ex vivo and subsequently reintroduced within the context of the current invention. Although the word "lymphocyte" is used, this also includes heterogenous cells that have been expanded during the ex vivo culturing process including dendritic cells, NKT cells, gamma delta T cells, and various other innate and adaptive immune cells.

As used herein, "cancer" refers to all types of cancer or neoplasm or malignant tumors found in animals, including leukemias, carcinomas and sarcomas. Examples of cancers are cancer of the brain, melanoma, bladder, breast, cervix, colon, head and neck, kidney, lung, non-small cell lung, mesothelioma, ovary, prostate, sarcoma, stomach, uterus and Medulloblastoma.

The term "leukemia" is meant broadly progressive, malignant diseases of the hematopoietic organs/systems and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemi.

The term "carcinoma" refers to a malignant new growth made up of epithelial cells tending to infiltrate the surrounding tissues, and/or resist physiological and non-physiological cell death signals and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrmcous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, and carcinoma scroti.

The term "sarcoma" generally refers to a tumor which is made up of a substance like the embryonic connective tissue and is generally composed of closely packed cells embedded in a fibrillar, heterogeneous, or homogeneous substance. Sarcomas include, chondrosarcoma, fibrosarcoma, lymphosarcoma, melanosarcoma, myxosarcoma, osteosarcoma, endometrial sarcoma, stromal sarcoma, Ewing's sarcoma, fascia! sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, choriocarcinoma, embryonal sarcoma, Wilns' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma. Additional exemplary neoplasias include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some particular embodiments of the invention, the cancer treated is a melanoma. The term "melanoma" is taken to mean a tumor arising from the melanocytic system of the skin and other organs. Melanomas include, for example, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

The term "polypeptide" is used interchangeably with "peptide", "altered peptide ligand", and "flourocarbonated peptides."

The term "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

The term "T cell" is also referred to as T lymphocyte, and means a cell derived from thymus among lymphocytes involved in an immune response. The T cell includes any of a CD8-positive T cell (cytotoxic T cell: CTL), a CD4-positive T cell (helper T cell), a suppressor T cell, a regulatory T cell such as a controlling T cell, an effector cell, a naive T cell, a memory T cell, an αβT cell expressing TCR α and β chains, and a γδ T cell expressing TCR γ and δ chains. The T cell includes a precursor cell of a T cell in which differentiation into a T cell is directed.

Examples of "cell populations containing T cells" include, in addition to body fluids such as blood (peripheral blood, umbilical blood etc.) and bone marrow fluids, cell populations containing peripheral blood mononuclear cells (PBMC), hematopoietic cells, hematopoietic stem cells, umbilical blood mononuclear cells etc., which have been collected, isolated, purified or induced from the body fluids. Further, a variety of cell populations containing T cells and derived from hematopoietic cells can be used in the present invention. These cells may have been activated by cytokine such as IL-2 in vivo or ex vivo. As these cells, any of cells collected from a living body, or cells obtained via ex vivo culture, for example, a T cell population obtained by the method of the present invention as it is, or obtained by freeze preservation, can be used.

The term "antibody" is meant to include both intact molecules as well as fragments thereof that include the antigen-binding site. Whole antibody structure is often given as H2L2 and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contains the amino acid sequences capable of specifically binding to antigenic targets. Within these sequences are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure. The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The antibodies disclosed according to the invention may also be wholly synthetic, wherein the polypeptide chains of the antibodies are synthesized and, possibly, optimized for binding to the polypeptides disclosed herein as being receptors. Such antibodies may be chimeric or humanized antibodies and may be fully tetrameric in structure, or may be dimeric and comprise only a single heavy and a single light chain.

The term "effective amount" or "therapeutically effective amount" means a dosage sufficient to treat, inhibit, or alleviate one or more symptoms of a disease state being treated or to otherwise provide a desired pharmacologic and/or physiologic effect, especially enhancing T cell response to a selected antigen. The precise dosage will vary according to a variety of factors such as subject-dependent variables (e.g., age, immune system health, etc.), the disease, and the treatment being administered.

The terms "individual", "host", "subject", and "patient" are used interchangeably herein, and refer to a mammal, including, but not limited to, primates, for example, human beings, as well as rodents, such as mice and rats, and other laboratory animals.

As used herein, the term "treatment regimen" refers to a treatment of a disease or a method for achieving a desired physiological change, such as increased or decreased response of the immune system to an antigen or immunogen, such as an increase or decrease in the number or activity of one or more cells, or cell types, that are involved in such response, wherein said treatment or method comprises administering to an animal, such as a mammal, especially a human being, a sufficient amount of two or more chemical agents or components of said regimen to effectively treat a disease or to produce said physiological change, wherein said chemical agents or components are administered together, such as part of the same composition, or administered separately and independently at the same time or at different times (i.e., administration of each agent or component is separated by a finite period of time from one or more of the agents or components) and where administration of said one or more agents or components achieves a result greater than that of any of said agents or components when administered alone or in isolation.

The term "anergy" and "unresponsiveness" includes unresponsiveness to an immune cell to stimulation, for example, stimulation by an activation receptor or cytokine. The anergy may occur due to, for example, exposure to an immune suppressor or exposure to an antigen in a high dose. Such anergy is generally antigen-specific, and continues even after completion of exposure to a tolerized antigen. For example, the anergy in a T cell and/or NK cell is characterized by failure of production of cytokine, for example, interleukin (IL)-2. The T cell anergy and/or NK cell anergy occurs in part when a first signal (signal via TCR or CD-3) is received in the absence of a second signal (costimulatory signal) upon exposure of a T cell and/or NK cell to an antigen.

The term "enhanced function of a T cell", "enhanced cytotoxicity" and "augmented activity" means that the effector function of the T cell and/or NK cell is improved. The enhanced function of the T cell and/or NK cell, which does not limit the present invention, includes an improvement in the proliferation rate of the T cell and/or NK cell, an increase in the production amount of cytokine, or an improvement in cytotoxity. Further, the enhanced function of the T cell and/or NK cell includes cancellation and suppression of tolerance of the T cell and/or NK cell in the suppressed state such as the anergy (unresponsive) state, or the rest state, that is, transfer of the T cell and/or NK cell from the suppressed state into the state where the T cell and/or NK cell responds to stimulation from the outside.

The term "expression" means generation of mRNA by transcription from nucleic acids such as genes, polynucleotides, and oligonucleotides, or generation of a protein or a polypeptide by transcription from mRNA. Expression may be detected by means including RT-PCR, Northern Blot, or in situ hybridization.

"Suppression of expression" refers to a decrease of a transcription product or a translation product in a significant amount as compared with the case of no suppression. The suppression of expression herein shows, for example, a decrease of a transcription product or a translation product in an amount of 30% or more, preferably 50% or more, more preferably 70% or more, and further preferably 90% or more.

In one embodiment of the invention the CAR-DC are antigen-loaded and co-cultured with T-lymphocytes to produce antigen-specific T-cells. As used herein, the term "antigen-specific T-cells" refers to T-cells that proliferate upon exposure to the antigen-loaded APCs of the present invention, as well as to develop the ability to attack cells having the specific antigen on their surfaces. Such T-cells, e.g., cytotoxic T-cells, lyse target cells by a number of methods, e.g., releasing toxic enzymes such as granzymes and perforin onto the surface of the target cells or by effecting the entrance of these lytic enzymes into the target cell interior. Generally, cytotoxic T-cells express CD8 on their cell surface. T-cells that express the CD4 antigen CD4, commonly known as "helper" T-cells, can also help promote specific cytotoxic activity and may also be activated by the antigen-loaded APCs of the present invention. In certain embodiments, the cancer cells, the APCs and even the T-cells can be derived from the same donor whose MNC yielded the DC, which can be the patient or an HLA—or obtained from the individual patient that is going to be treated. Alternatively, the cancer cells, the APCs and/or the T-cells can be allogeneic.

The invention provides means of inducing an anti-cancer response in a mammal, comprising the steps of initially "priming" the mammal by administering an agent that causes local accumulation of CAR-DC. Subsequently, a tumor antigen is administered in the local area where said agents causing accumulation of antigen presenting cells is administered. A time period is allowed to pass to allow for said antigen presenting cells to traffic to the lymph nodes. Subsequently a maturation signal, or a plurality of maturation signals are administered to enhance the ability of said antigen presenting cell to activate adaptive immunity. In some embodiments of the invention activators of adaptive immunity are concurrently given, as well as inhibitors of the tumor derived inhibitors are administered to derepress the immune system.

In one embodiment priming of the patient is achieved by administration of GM-CSF subcutaneously in the area in which antigen is to be injected. Various scenarios are known in the art for administration of GM-CSF prior to administration, or concurrently with administration of antigen. The practitioner of the invention is referred to the following publications for dosage regimens of GM-CSF and also of peptide antigens.

Subsequent to priming, the invention calls for administration of tumor antigen. Various tumor antigens may be utilized, in one preferred embodiment, lysed tumor cells from the same patient area utilized. Means for generation of lyzed tumor cells are well known in the art and described in the following references. One example method for generation of tumor lysate involves obtaining frozen autologous samples which are placed in hanks buffered saline solution (HBSS) and gentamycin 50 µg/ml followed by homogenization by a glass homogenizer. After repeated freezing and thawing, particle-containing samples are selected and frozen in aliquots after radiation with 25 kGy. Quality assessment for sterility and endotoxin content is performed before freezing. Cell lysates are subsequently administered into the patient in a preferred manner subcutaneously at the local areas where DC priming was initiated. After 12-72 hours, the patient is subsequently administered with an agent capable of inducing maturation of DC. Agents useful for the practice of the invention, in a preferred embodiment include BCG and HMGB1 peptide. Other useful agents include: a) histone DNA; b) inniqimod; c) beta-glucan; d) hsp65; e) hsp90; f) HMGB-1; g) lipopolysaccharide; h) Pam3CSK4; i) Poly I: Poly C; j) Flagellin; k) MALP-2; l) Imidazoquinoline; m) Resiquimod; n) CpG oligonucleotides; o) zymosan; p) peptidoglycan; q) lipoteichoic acid; r) lipoprotein from gram-positive bacteria; s) lipoarabinomannan from mycobacteria; t) Polyadenylic-polyuridylic acid; u) monophosphoryl lipid A; v) single stranded RNA; w) double stranded RNA; x) 852A; y) rintatolimod; z) Gardiquimod; and aa)

lipopolysaccharide peptides. The procedure is performed in a preferred embodiment with the administration of IDO silencing siRNA or shRNA containing the effector sequences a) UUAUAAUGACUGGAUGUUC (SEQ ID NO: 40); b) GUCUGGUGUAUGAAGGGUU (SEQ ID NO: 41); c) CUCCUAUUUUGGUUUAUGC (SEQ ID NO: 42) and d) GCAGCGUCUUUCAGUGCUU (SEQ ID NO: 43). siRNA or shRNA may be administered through various modalities including biodegradable matrices, pressure gradients or viral transfect. In another embodiment, autologous dendritic cells are generated and IDO is silenced, prior to, concurrent with or subsequent to silencing, said dendritic cells are pulsed with tumor antigen and administered systemically.

In one embodiment of the invention mature DC are modified with CAR transfection prior to administration. Culture of dendritic cells is well known in the art, for example, U.S. Pat. No. 6,936,468, issued to Robbins, et al., for the use of tolerogenic dendritic cells for enhancing tolerogenicity in a host and methods for making the same. Although the current invention aims to reduce tolerogenesis, the essential means of dendritic cell generation are disclosed in the patent. U.S. Pat. No. 6,734,014, issued to Hwu, et al., for methods and compositions for transforming dendritic cells and activating T cells. Briefly, recombinant dendritic cells are made by transforming a stem cell and differentiating the stem cell into a dendritic cell. The resulting dendritic cell is said to be an antigen presenting cell which activates T cells against MHC class I-antigen targets. Antigens for use in dendritic cell loading are taught in, e.g., U.S. Pat. No. 6,602,709, issued to Albert, et al. This patent teaches methods for use of apoptotic cells to deliver antigen to dendritic cells for induction or tolerization of T cells. The methods and compositions are said to be useful for delivering antigens to dendritic cells that are useful for inducing antigen-specific cytotoxic T lymphocytes and T helper cells. The disclosure includes assays for evaluating the activity of cytotoxic T lymphocytes. The antigens targeted to dendritic cells are apoptotic cells that may also be modified to express non-native antigens for presentation to the dendritic cells. The dendritic cells are said to be primed by the apoptotic cells (and fragments thereof) capable of processing and presenting the processed antigen and inducing cytotoxic T lymphocyte activity or may also be used in vaccine therapies. U.S. Pat. No. 6,455,299, issued to Steinman, et al., teaches methods of use for viral vectors to deliver antigen to dendritic cells. Methods and compositions are said to be useful for delivering antigens to dendritic cells, which are then useful for inducing T antigen specific cytotoxic T lymphocytes. The disclosure provides assays for evaluating the activity of cytotoxic T lymphocytes. Antigens are provided to dendritic cells using a viral vector such as influenza virus that may be modified to express non-native antigens for presentation to the dendritic cells. The dendritic cells are infected with the vector and are said to be capable of presenting the antigen and inducing cytotoxic T lymphocyte activity or may also be used as vaccines.

Immune cells for use in the practice of the invention include DCs, the presence of which may be checked in the previously described method, are preferably selected from myeloid cells (such as monocytic cells and macrophages) expressing langerin, MHC (major histocompatibility complex) class II, CCR2 (chemokine (C--C motif) receptor 2), CX3CR1 and/or Gr1 molecules in mice; myeloid cells expressing CD14, CD16, HLA dR (human leukocyte antigen disease resistance) molecule, langerin, CCR2 and/or CX3CR1 in humans; dendritic cells expressing CD11c, MHC class II molecules, and/or CCR7 molecules; and IL-1β producing dendritic cells. CD8 T cells, the presence of which may be checked in the previously described method, are preferably selected from CD3+, CD4+and/or CD8+T lymphocytes, FOXP3 (forkhead box P3) T lymphocytes, Granzyme B/TIA (Tcell-restricted intracellular antigen) T lymphocytes, and Tc1 cells (IFN-.gamma. producing CD8+T lymphocytes). Immune cells expressing a protein that binds calreticulin, such immune cells may be selected from cells expressing at least one of the following proteins: LRP1 (Low density lipoprotein receptor-related protein 1, CD91), Ca.sup.++-binding proteins such as SCARF1 and SCARF2, MSR1 (Macrophage scavenger receptor 1), SRA, CD59 (protectin), CD207 (langerin), and THSD1 (thrombospondin). There are numerous means known in the art to identify cells expressing various antigens, these include immunochemistry, immunophenotyping, flow cytometry, Elispots assays, classical tetramer staining, and intracellular cytokine stainings.

Macrophages selectively phagocytose tumor cells, but this process is countered by protective molecules on tumor cells such as CD47, which binds macrophage signal-regulatory protein a to inhibit phagocytosis. Blockade of CD47 on tumor cells leads to phagocytosis by macrophages. In one embodiment of the invention CAR-MSC are administered together with an agent that blocks CD47 activity. It has been demonstrated that activation of TLR signaling pathways in macrophages synergizes with blocking CD47 on tumor cells to enhance tumor phagocytosis. Bruton's tyrosine kinase (Btk) mediates TLR signaling in macrophages. Calreticulin, previously shown to be a protein found on cancer cells that activated macrophage phagocytosis of tumors, is activated in macrophages for secretion and cell-surface exposure by TLR and Btk to target cancer cells for phagocytosis, even if the cancer cells themselves do not express calreticulin. In one embodiment of the invention TLR agonists are administered that stimulate expression of calreticulin and/or enhance macrophage phagocytosis of tumors.

IL-27 induces macrophage ability to kill tumor cells in vitro and in vivo, as well as altering the tumor promoting M2/myeloid suppressor cells into tumoricidal cells. In one embodiment of the invention addition of IL-27 or compounds capable of activating the IL-27 receptor signaling are administered together with IL-27 to enhance tumor phagocytosis by macrophages.

Tumor-associated macrophages, deriving from monocytes or migrating into the tumor, are an important constituent of tumor microenvironments, which in many cases modulates tumor growth, tumor angiogenesis, immune suppression, metastasis and chemoresistance. Mechanisms of macrophage promotion of tumor growth include production of EGF, M-CSF, VEGF.

Macrophage infiltration of tumors is associated with poor prognosis in renal, melanoma, breast, pancreatic, lung, endometrial, bladder, prostate.

Tumor growth are inhibited when monocytes/macrophages are ablated. There is ample evidence that many anticancer modalities currently used in the clinic have unique and distinct properties that modulate the recruitment, polarization and tumorigenic activities of macrophages in the tumor microenvironments. By manipulating tumor-associated macrophages significant impact on the clinical efficacies of and resistance to these anticancer modalities. Accordingly, in one aspect of the invention, CAR-DC, CAR-monocytes, or CAR-macrophages are utilized to force the tumor microenvironment to stimulate tumor killing and inhibit macrophage or macrophage related cells from promoting tumor growth. Within the context of the invention, the use of drugs targeting tumor-associated macrophages, especially c-Fms kinase inhibitors and humanized antibodies targeting colony-stimulating factor-1 receptor, are envisioned.

Tumors mediate various effects to reprogram macrophages, these are usually mediated via IL-10 and other cytokines such as VEGF, TGF-beta, and M-CSF, which cause macrophages to lose tumor cytotoxicity and shift into tumor promoting, immune suppressive, angiogenic supporting cells. Related to tumor manipulated monocytes are myeloid derived suppressor cells, which are similar to myeloid progenitor cells, or the previously described "natural suppressor" cell.

Irradiated tissues induce a TLR-1 reprogramming of macrophages to promote tumor growth and angiogenesis. Macrophage promotion of tumor growth is seen in numerous situations, in one example, treating of tumor bearing animals with BRAF inhibitors results in upregulation of macrophage production of VEGF which accelerates tumor growth. Mechanistically, it is known that tumors produce factors such as GM-CSF which in part stimulate macrophages to produce CCL18, which promotes tumor metastasis. Additionally, the lactic acid microenvironment of the tumor has been shown to promote skewing of macrophages towards at tumor-promoting M2 type. It has been shown that lactic acid produced by tumour cells, as a by-product of aerobic or anaerobic glycolysis, possesses an essential role in inducing the expression of VEGF and the M2-like polarization of tumour-associated macrophages, specifically inducing expression of arginase 1 through a HIF-1alpha dependent pathway. Mechanistically, it is known that lactic acid in tumors is generated in a large part by lactate dehydrogenase-A (LDH-A), which converts pyruvate to lactate. siRNA silencing of LDH-A in Pan02 pancreatic cancer cells that are injected in C57BL/6 mice results in development of smaller tumors than mice injected with wild type, non-silenced Pan02 cells. Associated with the reduced tumor growth were observations of a decrease in the frequency of myeloid-derived suppressor cells (MDSCs) in the spleens of mice carrying LDH-A-silenced tumors. NK cells from LDH-A-depleted tumors had improved cytolytic function. Exogenous lactate administration was shown to increase the frequency of MDSCs generated from mouse bone marrow cells with GM-CSF and IL-6 in vitro. Furthermore lactate pretreatment of NK cells in vitro inhibited cytolytic function of both human and mouse NK cells. This reduction of NK cytotoxic activity was accompanied by lower expression of perforin and granzyme in NK cells. The expression of NKp46 was lower in lactate-treated NK cells. Accordingly, in one embodiment of the invention, depletion of glucose levels using a ketogenic diet to lower lactate production by glycolytic tumors is utilized to augment therapeutic effects of CAR-DC. Utilization of ketogenic diet has been previously described for immune modulation, and cancer therapy. Specific quantification of intratumoral lactate and its manipulation has been described and incorporated by reference. Potentiation of chemotherapeutic and radiotherapeutic effects by ketogenic diets have been reported and techniques are incorporated by reference for use with the current CAR-DC invention. Suppression of tumor growth and activity induced by ketogenic diet may be augmented by addition of hyperbaric oxygen, thus in one embodiment of the invention, the utilization of oxidative therapies, as disclosed in references incorporated, together with ketogenic diet is utilized to augment therapeutic efficacy of CAR-DC.

Not only has it been well known that monocytes and macrophages infiltrate tumors and appear to support tumor growth through growth factor production and secretion of angiogenic agents, but suggestions have been made that tumors themselves, as part of the epithelial mesenchymal transition may actually differentiate into monocytes in part associated with TGF-beta production. Specifically, a study reported performing gene-profiling analysis of mouse mammary EpRas tumor cells that had been allowed to adopt an epithelial to mesenchymal transition program after long-term treatment with TGF-131 for 2 weeks. While the treated cells acquired traits of mesenchymal cell differentiation and migration, gene analysis revealed another cluster of induced genes, which was specifically enriched in monocyte-derived macrophages, mast cells, and myeloid dendritic cells, but less in other types of immune cells. Further studies revealed that this monocyte/macrophage gene cluster was enriched in human breast cancer cell lines displaying an EMT or a Basal B profile, and in human breast tumors with EMT and undifferentiated (ER-/PR) characteristics. The plasticity of tumor cells to potentially monocytic lineages should come as no surprise given that tumor cells have been shown to differentiate directly into pericytes, and endothelial cells/vascular channels.

Dopamine possesses antiangiogenic effects as well as myeloprotective effects, in one embodiment of the invention addition of dopamine to the CAR-DC treatment is disclosed.

Vinblastine is a widely used chemotherapeutic agent that has been demonstrated to induce dendritic cell maturation. In one embodiment of the invention CAR-DC are utilized together with vinblastine therapy to induce augmented anticancer activity. Oxiplatin and anthracyclines have been demonstrated to not only directly kill tumor cells but also stimulate T cell immunity against tumor cells. It was demonstrated that these agents induce a rapid and prominent invasion of interleukin (IL)-17 producing γδ (Vy4(+) and Vy6(+)) T lymphocytes (γδ T17 cells) that precedes the accumulation of CD8 CTLs within the tumor bed. In T cell receptor δ(-/-) or Vy4/6(-/-) mice, the therapeutic efficacy of chemotherapy was reduced and furthermore no IL-17 was produced by tumor-infiltrating T cells, and CD8 CTLs did not invade the tumor after treatment. Although y6 Th17 cells could produce both IL-17A and IL-22, the absence of a functional IL-17A-IL-17R pathway significantly reduced tumor-specific T cell responses elicited by tumor cell death, and the efficacy of chemotherapy in four independent transplantable tumor models. The adoptive transfer of γδ T cells to naïve mice restored the efficacy of chemotherapy in IL-17A(-/-) hosts. The anticancer effect of infused y6 T cells was lost when they lacked either IL-1R1 or IL-17A.

Intratumoral injection of dendritic cells stimulates antitumor immunity in vivo in clinical situations, suggesting that modulating the antigen presenting cell in the tumor microenvironment will induce an antitumor response. Administration of radiotherapy to tumors to induce immunogenic cell death, followed by intratumoral administration of DC has been demonstrated to result in enhanced antigen presentation, accordingly, this technique may be modified to enhance effects of CAR-DC. The induction of immunity to tumors in the present invention is associated with the unique nature of: a) ongoing basal cell death within the tumor; and b) cell death induced by chemotherapy, radiotherapy, hyperthermia, or otherwise induced cell death. Cell death can be classified according to the morphological appearance of the lethal process (that may be apoptotic, necrotic, autophagic or associated with mitosis), enzymological criteria (with and without the involvement of nucleases or distinct classes of proteases, like caspases), functional aspects (programmed or accidental, physiological or pathological) or immunological characteristics (immunogenic or non-immunogenic). Cell death is defined as "immunogenic" or "immune stimulatory" if dying cells that express a specific antigen (for example a tumor associated antigen, phosphotidyl serine, or calreticulin), yet are uninfected (and hence lack pathogen-associated molecular patterns), and are injected subcutaneously into mice, in the absence of any adjuvant, cause a protective immune response against said specific antigen. Such a protective immune response precludes the growth of living transformed cells expressing the specific antigen injected into mice. When cancer cells succumb to an immunogenic cell death (or immunogenic apoptosis) modality, they stimulate the immune system, which then mounts a therapeutic anti-cancer immune response and contributes to the eradication of residual tumor cells. Conversely, when cancer cells succumb to a non-immunogenic death modality, they fail to elicit such a protective immune response. Regardless of the types of cell death that are ongoing, the tumor derived immune suppressive molecules contribute to general inhibition or inability of the tumor to be eliminated.

Within the practice of the invention, CAR-DC are administered concurrently, prior to, or subsequent to administration of an agent that induces immunogenic cell death in a patient. Methods of determining whether compounds induce immunogenic cell death are known in the art and include the following, which was described by Zitvogel et al. (a) treating the cells, the mammalian cells and inducing the cell death or apoptosis, typically of mammalian cancer cells capable of expressing calreticulin (CRT), by exposing said mammalian cells to a particular drug (the test drug), for example 18 hours; (b) inoculating (for example intradermally) the dying mammalian cells from step (a) in a particular area (for example a flank) of the mammal, typically a mouse, to induce an immune response in this area of the mammal; (c) inoculating (for example intradermally) the minimal tumorigenic dose of syngeneic live tumor cells in a distinct area (for example the opposite flank) from the same mammal, for example 7 days after step (b); and (d) comparing the size of the tumor in the inoculated mammal with a control mammal also exposed to the minimal tumorigenic dose of syngeneic live tumor cells of step (c) [for example a mouse devoid of T lymphocyte], the stabilization or regression of the tumor in the inoculated mammal being indicative of the drug immunogenicity. Other in vitro means are available for assessing the ability of various drugs or therapeutic approaches to induce immunogenic cell death. Specific characteristics to assess when screening for immunogenic cell death include: a) ability to induce dendritic cell maturation in vitro; b) ability to activate NK cells; and c) ability to induce activation of gamma delta T cells or NKT cells. Specific drugs known to induce immunogenic cell death include oxiplatine and anthracyclines, as well as radiotherapy, and hyperthermia. In the case of chemotherapies, certain chemotherapies that activate TLR4 through induction of HMGB1 have been observed to function suboptimally in patients that have a TLR4 polymorphism, thus suggesting actual contribution of TLR activation as a means of chemotherapy inhibition of cancer. Additionally, oncoviruses or oncolytic viruses are known to induce immunogenic cell death and may be useful for the practice of the invention.

The CAR-DC disclosed in the invention may be utilized in combination with conventional immune modulators including BCG, CpG DNA, interferon alpha, tumor bacterial therapy, checkpoint inhibitors, Treg depleting agents, and low dose cyclophosphamide.

In one embodiment of the invention CAR-DC cells are generated with specificity towards ROBO-4. Numerous means of generating CAR-T cells are known in the art, which are applied to CAR-DC. In one embodiment of the invention FMC63-28z CAR (Genebank identifier HM852952.1), is used as the template for the CAR except the anti-CD19, single-chain variable fragment sequence is replaced with an ROBO-4 fragment. The construct is synthesized and inserted into a pLNCX retroviral vector. Retroviruses encoding the ROBO-4-specific CAR are generated using the retrovirus packaging kit, Ampho (Takara), following the manufacturer's protocol. For generation of CAR-DC cells donor blood is obtained and after centrifugation on Ficoll-Hypaque density gradients (Sigma-Aldrich), PBMCs are plated at 2×10(6) cells/mL in cell culture for 2 hours and the adherent cells are collected. The cells were then stimulated for 2 days on a tissue-culture-treated 24-well plate containing M-CSF at a concentration of 100 ng/ml For retrovirus transduction, a 24-well plate are coated with RetroNectin (Takara) at 4° C. overnight, according to the manufacturer's protocol, and then blocked with 2% BSA at room temperature for 30 min. The plate was then loaded with retrovirus supernatants at 300 μL/well and incubated at 37° C. for 6 h. Next, 1×10(6) stimulated adherent cells in 1 mL of medium are added to 1 mL of retrovirus supernatants before being transferred to the pre-coated wells and cultured at 37° C. for 2 d. The cells are then transferred to a tissue-culture-treated plate at 1×10 (6)cells/mL and cultured in the presence of 100 U/mL of recombinant human M-CSF, applying the T cell protocol but not utilizing IL-2 or antiCD3/antiCD28.

Other means of generating CARs are known in the art and incorporated by reference. For example, Groner's group genetically modified T lymphocytes and endowed them with the ability to specifically recognize cancer cells. Tumor cells overexpressing the ErbB-2 receptor served as a model. The target cell recognition specificity was conferred to T lymphocytes by transduction of a chimeric gene encoding the zeta-chain of the TCR and a single chain antibody (scFv (FRP5)) directed against the human ErbB-2 receptor. The chimeric scFv(FRP5)-zeta gene was introduced into primary mouse T lymphocytes via retroviral gene transfer. Naive T lymphocytes were activated and infected by cocultivation with a retrovirus-producing packaging cell line. The scFv (FRP5)-zeta fusion gene was expressed in >75% of the T cells. These T cells lysed ErbB-2-expressing target cells in vitro with high specificity. In a syngeneic mouse model, mice were treated with autologous, transduced T cells. The adoptively transferred scFv(FRP5)-zeta-expressing T cells caused total regression of ErbB-2-expressing tumors. The presence of the transduced T lymphocytes in the tumor tissue was monitored. No humoral response directed against the transduced T cells was observed. Abs directed against the ErbB-2 receptor were detected upon tumor lysis. Hombach et al. constructed an anti-CEA chimeric receptor whose extracellular moiety is composed of a humanized scFv derived from the anti-CEA mAb BW431/26 and the CH2/CH3 constant domains of human IgG. The intracellular moiety consists of the gamma-signaling chain of the human Fc epsilon RI receptor constituting a completely humanized chimeric receptor. After transfection, the humBW431/26 scFv-CH2CH3-gamma receptor is expressed as a homodimer on the surface of MD45 T cells. Co-incubation with CEA+ tumor cells specifically activates grafted MD45 T cells indicated by IL-2 secretion and cytolytic activity against CEA+ tumor cells. Notably, the efficacy of receptor-mediated activation is not affected by soluble CEA up to 25 micrograms/ml demonstrating the usefulness of this chimeric receptor for specific cellular activation by membrane-bound CEA even in the presence of high concentrations of CEA, as found in patients during progression of the disease (200). These methods are described to guide one of skill in the art to practicing the invention, which in one embodiment is the utilization of CAR T cell approaches towards targeting tumor endothelium as comparted to simply targeting the tumor itself.

Targeting of mucins associated with cancers has been performed with CAR T cells by grafting the antibody that binds to the mucin with CD3 zeta chain. For the purpose of the invention, this procedure is modified for CAR-DC. In an older publication chimeric immune receptor consisting of an extracellular antigen-binding domain derived from the CC49 humanized single-chain antibody, linked to the CD3zeta signaling domain of the T cell receptor, was generated (CC49-zeta). This receptor binds to TAG-72, a mucin antigen expressed by most human adenocarcinomas. CC49-zeta was expressed in CD4+ and CD8+ T cells and induced cytokine production on stimulation. Human T cells expressing CC49-zeta recognized and killed tumor cell lines and primary tumor cells expressing TAG-72. CC49-zeta T cells did not mediate bystander killing of TAG-72-negative cells. In addition, CC49-zeta T cells not only killed FasL-positive tumor cells in vitro and in vivo, but also survived in their presence, and were immunoprotective in intraperitoneal and subcutaneous murine tumor xenograft models with TAG-72-positive human tumor cells. Finally, receptor-positive T cells were still effective in killing TAG-72-positive targets in the presence of physiological levels of soluble TAG-72, and did not induce killing of TAG-72-negative cells under the same conditions.

For clinical practice of the invention several reports exist in the art that would guide the skilled artisan as to concentrations, cell numbers, and dosing protocols useful. While in the art CAR T cells have been utilized targeting surface tumor antigens, the main issue with this approach is the difficulty of T cells to enter tumors due to features specific to the tumor microenvironment. These include higher interstitial pressure inside the tumor compared to the surroundings, acidosis inside the tumor, and expression in the tumor of FasL which kills activated T cells. Accordingly the invention seeks to more effectively utilize CAR-DC cells by directly targeting them to tumor endothelium, which is in direct contact with blood and therefore not susceptible to intratumoral factors the limit efficacy of conventional T cell therapies. In other embodiments CAR-DC are targeting to tumor antigens.

In one embodiment of the invention, protocols similar to Kershaw et al. are utilized with the exception that tumor endothelial antigens are targeted as opposed to conventional tumor antigens. Such tumor endothelial antigens include CD93, TEM-1, VEGFR1, and survivin. Antibodies can be made for these proteins, methodologies for which are described in U.S. Pat. Nos. 5,225,539, 5,585,089, 5,693,761, and 5,639,641. In one example that may be utilized as a template for clinical development, T cells with reactivity against the ovarian cancer-associated antigen alpha-folate receptor (FR) were generated by genetic modification of autologous T cells with a chimeric gene incorporating an anti-FR single-chain antibody linked to the signaling domain of the Fc receptor gamma chain. Patients were assigned to one of two cohorts in the study. Eight patients in cohort 1 received a dose escalation of T cells in combination with high-dose interleukin-2, and six patients in cohort 2 received dual-specific T cells (reactive with both FR and allogeneic cells) followed by immunization with allogeneic peripheral blood mononuclear cells. Five patients in cohort 1 experienced some grade 3 to 4 treatment-related toxicity that was probably due to interleukin-2 administration, which could be managed using standard measures. Patients in cohort 2 experienced relatively mild side effects with grade 1 to 2 symptoms. No reduction in tumor burden was seen in any patient. Tracking 111In-labeled adoptively transferred T cells in cohort 1 revealed a lack of specific localization of T cells to tumor except in one patient where some signal was detected in a peritoneal deposit. PCR analysis showed that gene-modified T cells were present in the circulation in large numbers for the first 2 days after transfer, but these quickly declined to be barely detectable 1 month later in most patients. Similar CAR-T clinical studies have been reported for neuroblastoma, B cell malignancies, melanoma, ovarian cancer, renal cancer, mesothelioma, and head and neck cancer.

In one embodiment of the invention, PBMCs are derived from leukapheresis and CD14 monocytes are collected by MACS. After 3 days of culture, M-CSF at 100 ng/ml plasmid encoding the chimeric CAR-DC recognizing tumor-endothelium specific antigen and subsequently selected for gene integration by culture in G418. In another embodiment the generation of dual-specific T cells is performed, stimulation of allogeneic monocytic cells is achieved by coculture of patient PBMCs with irradiated (5,000 cGy) allogeneic donor PBMCs from cryopreserved apheresis product (mixed lymphocyte reaction). The MHC haplotype of allogeneic donors is determined before use, and donors that differed in at least four MHC class I alleles from the patient are used. Culture medium consisted of AimV medium (Invitrogen, Carlsbad, CA) supplemented with 5% human $AB^-$ serum (Valley Biomedical, Winchester, VA), penicillin (50 units/mL), streptomycin (50 mg/mL; Bio Whittaker, Walkersville, MD), amphotericin B (Fungizone, 1.25 nng/mL, Biofluids, Rockville, MD), L-glutamine (2 mmol/L; Mediatech, Herndon, VA), and human recombinant IL-2 (Proleukin, 300 IU/mL; Chiron). Mixed lymphocyte reaction consisted of $2\times10^6$ patient monocytes and $1\times10^7$ allogeneic stimulator PBMCs in 2 mL AimV per well in 24-well plates. Between 24 and 48 wells are cultured per patient for 3 days, at which time transduction is done by aspirating 1.5 mL of medium and replacing with 2.0 mL retroviral supernatant containing 300 IU/mL IL-2, 10 mmol/L HEPES, and 8 µg/mL polybrene (Sigma, St. Louis, MO) followed by covering with plastic wrap and centrifugation at 1,000×g for 1 hour at room temperature. After overnight culture at 37° C./5% $CO_2$, transduction is repeated on the following day, and then medium was replaced after another 24 hours. Cells are then resuspended at $1\times10^6$/mL in fresh medium containing 0.5 mg/mL G418 (Invitrogen) in 175-cm² flasks for 5 days before resuspension in media lacking G418. 'Cells are expanded to $2\times10^9$ and then restimulated with allogeneic PBMCs from the same donor to enrich for T cells specific for the donor allogeneic haplotype. Restimulation is done by incubating patient T cells ($1\times10^6$/mL) and stimulator PBMCs ($2\times10^6$/mL) in 3-liter Fenwall culture bags in AimV+additives and IL-2 (no G418). Cell numbers were adjusted to $1\times10^6$/mL, and IL-2 was added every 2 days, until sufficient numbers for treatment were achieved.

The present invention relates to a strategy of adoptive cell transfer of monocytes or DC transduced to express a chimeric antigen receptor (CAR). CARs are molecules that combine antibody-based specificity for a desired antigen (e.g., tumor endothelial antigen) with a T cell receptor-activating intracellular domain to generate a chimeric protein that exhibits a specific anti-tumor endothelium cellular immune activity. In one embodiment the present invention relates generally to the use of monocytes or DC cells genetically modified to stably express a desired CAR that possesses high affinity towards tumor associated endothelium. Monocytes or DC cells expressing a CAR are referred to herein as CAR-DC cells or CAR modified DC cells. Preferably, the cell can be genetically modified to stably express an antibody binding domain on its surface, conferring novel antigen specificity that is MHC independent. In some instances, the monocyte or DC cell is genetically modified to stably express a CAR that combines an antigen recognition domain of a specific antibody with an intracellular domain of the CD3-zeta chain or Fc.gamma.RI protein into a single chimeric protein. In another embodiment, TLR signaling molecules are engineered in the intracellular portion of the CAR, said molecules include TRIF, TRADD, and MyD99. In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. Preferably, the transmembrane domain is the CD8a hinge domain.

With respect to the cytoplasmic domain, the CAR of the invention can be designed to comprise the CD80 and/or CD86 and/or CD40L and/or OX40L signaling domain by itself or be combined with any other desired cytoplasmic domain(s) useful in the context of the CAR of the invention. In one embodiment, the cytoplasmic domain of the CAR can be designed to further comprise the signaling domain of MyD88. For example, the cytoplasmic domain of the CAR can include but is not limited to CD80 and/or CD86 and/or CD40L and/or OX40L signaling modules and combinations thereof. In another embodiment of the invention inhibition of TGF-beta is performed either by transfection with an shRNA possessing selectively towards TGF-beta or by constructing the CAR to possess a dominant negative mutant of TGF-beta receptor. This would render the CAR-DC cell resistant to inhibitory activities of the tumors. Accordingly, the invention provides CAR-DC cells and methods of their use for adoptive therapy. In one embodiment, the CAR-DC cells of the invention can be generated by introducing a lentiviral vector comprising a desired CAR, for example a CAR comprising anti-CD19, CD8a hinge and transmembrane domain, and MyD88, into the cells. The CAR-DC cells of the invention are able to replicate in vivo resulting in long-term persistence that can lead to sustained tumor control.

One skilled in the art will appreciate that these methods, compositions, and cells are and may be adapted to carry out the objects and obtain the ends and advantages mentioned, as well as those inherent therein. The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. It will be apparent to one skilled in the art that varying substitutions and modifications may be made to the invention disclosed herein without departing from the scope and spirit of the invention. Those skilled in the art recognize that the aspects and embodiments of the invention set forth herein may be practiced separate from each other or in conjunction with each other. Therefore, combinations of separate embodiments are within the scope of the invention as disclosed herein. All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

The invention claimed is:

1. A pharmaceutical composition comprising:
(a) an ex vivo population of cells comprising CD14+/CD16+ cells, wherein the CD14+/CD16+ cells comprise a recombinant polynucleic acid with a sequence encoding a chimeric antigen receptor (CAR), wherein the CAR comprises (i) an anti-HER2/neu binding domain and a CD8a hinge domain; (ii) a transmembrane domain; and (iii) an intracellular domain containing a CD3 zeta intracellular signaling domain; and
(b) a pharmaceutically acceptable excipient;
wherein the pharmaceutical composition stimulates tumor killing by T cells in a subject with cancer when the pharmaceutical composition is administered to the subject.

2. The pharmaceutical composition of claim 1, wherein the transmembrane domain comprises a CD8a transmembrane domain.

3. The pharmaceutical composition of claim 1, wherein the intracellular domain comprises two or more intracellular signaling domains.

4. The pharmaceutical composition of claim 1, wherein the ex vivo population of cells is an ex vivo population of virally transduced cells.

5. The pharmaceutical composition of claim 1, wherein the CD14+/CD16+ cells comprise a viral component.

6. The pharmaceutical composition of claim 1, wherein the sequence of the recombinant polynucleic acid encoding the CAR is from a viral vector.

7. The pharmaceutical composition of claim 1, wherein the ex vivo population of cells consists of CD14+/CD16+ cells.

8. The pharmaceutical composition of claim 1, wherein the ex vivo population of cells is from a human subject.

9. The pharmaceutical composition of claim 8, wherein the ex vivo population of cells is from a leukapheresis sample, a blood sample, or a PBMC sample from the human subject.

10. The pharmaceutical composition of claim 8, wherein the human subject has cancer.

11. The pharmaceutical composition of claim 10, wherein the cancer is a lymphoma or a solid tumor.

12. The pharmaceutical composition of claim 11, wherein the cancer is breast cancer or metastatic cancer.

13. The pharmaceutical composition of claim 10, wherein the cancer is an ErbB-2-expressing cancer.

14. The pharmaceutical composition of claim 1, wherein the anti-HER2/neu binding domain is a single chain variable fragment (scFv).

15. The pharmaceutical composition of claim 1, wherein the anti-HER2/neu binding domain is a single domain antibody (sdAb).

16. The pharmaceutical composition of claim 1, wherein the CD14+/CD16+ cells are phagocytic CD14+/CD16+ cells.

17. The pharmaceutical composition of claim 1, wherein the CD14+/CD16+ cells are human CD14+/CD16+ cells.

18. The pharmaceutical composition of claim 1, wherein the CD14+/CD16+ cells are isolated CD14+/CD16+ cells.

19. The pharmaceutical composition of claim 1, wherein the CD14+/CD16+ cells are monocytes.

20. The pharmaceutical composition of claim 1, wherein the CD14+/CD16+ cells are dendritic cells.

21. The pharmaceutical composition of claim 1, wherein the CD14+/CD16+ cells are macrophages.

22. The pharmaceutical composition of claim 1, wherein the recombinant polynucleic acid is RNA.

23. The pharmaceutical composition of claim 22, wherein the recombinant polynucleic acid is mRNA.

24. The pharmaceutical composition of claim 1, wherein the recombinant polynucleic acid is from a viral vector.

25. The pharmaceutical composition of claim 1, wherein the CAR consists of an anti-HER2/neu binding domain, a CD8a hinge domain, a CD8a transmembrane domain,
and an intracellular domain containing a CD3 zeta intracellular signaling domain.

26. The pharmaceutical composition of claim 1, wherein the ex vivo population of cells comprises at least $1\times10^{6}$ CD14+/CD16+ cells.

27. The pharmaceutical composition of claim 1, wherein the intracellular domain of the CAR is capable of inducing monocytic differentiation to M1 macrophages when the pharmaceutical composition is administered to a subject.

28. The pharmaceutical composition of claim 1, wherein the CD14+/CD16+ cells of the pharmaceutical composition directly kill tumor cells when the pharmaceutical composition is administered to a subject with a tumor.

29. The pharmaceutical composition of claim 1, wherein the pharmaceutical composition enhances or improves effector function of a T cell in a subject when the pharmaceutical composition is administered to the subject.

30. The pharmaceutical composition of claim 1, wherein the pharmaceutical composition inhibits macrophage or macrophage related cells from promoting tumor growth when the pharmaceutical composition is administered to a subject with cancer.

* * * * *

SEQUENCE LISTING

```
Sequence total quantity: 43
SEQ ID NO: 1            moltype = AA    length = 757
FEATURE                 Location/Qualifiers
source                  1..757
                        mol_type = protein
                        organism = Homo sapiens
SEQUENCE: 1
MLLRLLLAWA AAGPTLGQDP WAAEPRAACG PSSCYALFPR RRTFLEAWRA CRELGGDLAT   60
PRTPEEAQRV DSLVGAGPAS RLLWIGLQRQ ARQCQLQRPL RGFTWTTGDQ DTAFTNWAQP  120
ASGGPCPAQR CVALEASGEH RWLEGSCTLA VDGYLCQFGF EGACPALQDE AGQAGPAVYT  180
TPFHLVSTEF EWLPFGSVAA VQCQAGRGAS LLCVKQPEGG VGWSRAGPLC LGTGCSPDNG  240
GCEHECVEEV DGHVSCRCTE GFRLAADGRS CEDPCAQAPC EQQCEPGGPQ GYSCHCRLGF  300
RPAEDDPHRC VDTDECQIAG VCQQMCVNYV GGFECYCSEG HELEADGISC SPAGAMGAQA  360
SQDLGDELLD DGEDEEDEDE AWKAFNGGWT EMPGILWMEP TQPPDFALAY RPSFPEDREP  420
QIPYPEPTWP PPLSAPRVPY HSSVLSVTRP VVVSATHPTL PSAHQPPVIP ATHPALSRDH  480
```

```
QIPVIAANYP DLPSAYQPGI LSVSHSAQPP AHQPPMISTK YPELFPAHQS PMFPDTRVAG   540
TQTTTHLPGI PPNHAPLVTT LGAQLPPQAP DALVLRTQAT QLPIIPTAQP SLTTTSRSPV   600
SPAHQISVPA ATQPAALPTL LPSQSPTNQT SPISPTHPHS KAPQIPREDG PSPKLALWLP   660
SPAPTAAPTA LGEAGLAEHS QRDDRWLLVA LLVPTCVFLV VLLALGIVYC TRCGPHAPNK   720
RITDCYRWVI HAGSKSPTEP MPPRGSLTGV QTCRTSV                            757

SEQ ID NO: 2             moltype = AA  length = 1443
FEATURE                  Location/Qualifiers
source                   1..1443
                         mol_type = protein
                         organism = Homo sapiens
SEQUENCE: 2
MSLLMFTQLL LCGFLYVRVD GSRLRQEDFP PRIVEHPSDV IVSKGEPTTL NCKAEGRPTP    60
TIEWYKDGER VETDKDDPRS HRMLLPSGSL FFLRIVHGRR SKPDEGSYVC VARNYLGEAV   120
SRNASLEVAL LRDDFRQNPT DVVVAAGEPA ILECQPPRGH PEPTIYWKKD KVRIDDKEER   180
ISIRGGKLMI SNTRKSDAGM YTCVGTNMVG ERDSDPAELT VFERPTFLRR PINQVVLEEE   240
AVEFRCQVQG DPQPTVRWKK DDADLPRGRY DIKDDYTLRI KKTMSTDEGT YMCIAENRVG   300
KMEASATLTV RARPVAPPQF VVRPRDQIVA QGRTVTFPCE TKGNPQPAVF WQKEGSQNLL   360
FPNQPQQPNS RCSVSPTGDL TITNIQRSDA GYYICQALTV AGSILAKQL EVTDVLTDRP    420
PPIILQGPAN QTLAVDGTAL LKCKATGDPL PVISWLKEGF TFPGRDPRAT IQEQGTLQIK   480
NLRISDTGTY TCVATSSSGE TSWSAVLDVT ESGATISKNY DLSDLPGPPS KPQVTDVTKN   540
SVTLSWQPGT PGTLPASAYI IEAFSQSVSN SWQTVANHVK TTLYTVRGLR PNTIYLFMVR   600
AINPQGLSDP SPMSDPVRTQ DISPPAQGVD HRQVQKELGD VLVRLHNPVV LTPTTVQVTW   660
TVDRQPQFIQ GYRVMYRQTS GLQATSSWQN LDAKVPTERS AVLVNLKKGV TYEIKVRPYF   720
NEFQGMDSES KTVRTTEEAP SAPPQSVTVL TVGSYNSTSI SVSWDPPPPD HQNGIIQEYK   780
IWCLGNETRF HINKTVEDAAI RSVIIGGLFP GIQYRVEVAA STSAGVGVKS EPQPIIIGRR   840
NEVVITENNN SITEQITDVV KQPAFIAGIG GACWVILMGF SIWLYWRRKK RKGLSNYAVT   900
FQRGDGGLMS NGSRPGLLNA GDPSYPWLAD SWPATSLPVN NSNSGPNEIG NFGRGDVLPP   960
VPGQGDKTAT MLSDGAIYSS IDFTTKTSYN SSSQITQATP YATTQILHSN SIHELAVDLP  1020
DPQWKSSIQQ KTDLMGFGYS LPDQNKGNNG GKGGKKKKNK SSKPQKNNG STWANVPLPP   1080
PPVQPLPGTE LEHYAVEQQE NGYDSDSWCP PLPVQTYLHQ GLEDELEEDD DRVPTPPVRG  1140
VASSPAISFG QQSTATLTPS PREEMQPMLQ AHLDELTRAY QFDIAKQTWH IQSNNQPPQP  1200
PVPPLGYVSG ALISDLETDV ADDDADDEEE ALEIPRPLRA LDQTPGSSMD NLDSSVTGSM  1260
VNGWGSASDE DRNFSSHRSS VGSSSDGSIF ASGSFAQALV AAADKAGFRL DGTSLTRTGK  1320
AFTSSQRPRP TSPFSTDSNT SAALSQSQRP RPTKKHKGGR MDQQPALPHR REGMTDEEAL  1380
VPYSKPSFPS PGGHSSSGTA SSKGSTGPRK TEVLRAGHQR NASDLLDIGY MGSNSQGQFT  1440
GEL                                                                1443

SEQ ID NO: 3             moltype = AA  length = 712
FEATURE                  Location/Qualifiers
source                   1..712
                         mol_type = protein
                         organism = Homo sapiens
SEQUENCE: 3
MQSKVLLAVA LWLCVETRAA SVGLPSVSLD LPRLSIQKDI LTIKANTTLQ ITCRGQRDLD    60
WLWPNNQSGS EQRVEVTECS DGLFCKTLTI PKVIGNDTGA YKCFYRETDL ASVIYVYVQD   120
YRSPFIASVS DQHGVVYITE NKNKTVVIPC LGSISNLNVS LCARYPEKRF VPDGNRISWD   180
SKKGFTIPSY MISYAGMVFC EAKINDESYQ SIMYIVVVVG YRIYDVVLSP SHGIELSVGE   240
KLVLNCTART ELNVGIDFNW EYPSSKHQHK KLVNRDLKTQ SGSEMKKFLS TLTIDGVTRS   300
DQGLYTCAAS SGLMTKKNST FVRVHEKPFV AFGSGMESLV EATVGERVRI PAKYLGYPPP   360
EIKWYKNGIP LESNHTIKAG HVLTIMEVSE RDTGNYTVIL TNPISKEKQS HVVSLVVYVP   420
PQIGEKSLIS PVDSYQYGTT QTLTCTVYAI PPPHHIHWYW QLEEECANEP SQAVSVTNPY   480
PCEEWRSVED PQGGNKIEVN KNQPFALIEGK NKTVSTLVIQ AANVSALYKC EAVNKVGRGE   540
RVISFHVTRG PEITLQPDMQ PTEQESVSLW CTADRSTFEN LTWYKLGPQP LPIHVGELPT   600
PVCKNLDTLW KLNATMFSNS TNDILIMELK NASLQDQGDY VCLAQDRKTK KRHCVVRQLT   660
VLERVAPTIT GNLENQTTSI GESIEVSCTA SGNPPPQIMF FKDNETLVED SE           712

SEQ ID NO: 4             moltype = AA  length = 658
FEATURE                  Location/Qualifiers
source                   1..658
                         mol_type = protein
                         organism = Homo sapiens
SEQUENCE: 4
MDRGTLPLAV ALLLASCSLS PTSLAETVHC DLQPVGPERG EVTYTTSQVS KGCVAQAPNA    60
ILEVHVLFLE FPTGPSQLEL TLQASKQNGT WPREVLLVLS VNSSVFLHLQ ALGIPLHLAY   120
NSSLVTFQEP PGVNTTELPS FPKTQILEWA AERGPITSAA ELNDPQSILL RLGQAQGSLS   180
FCMLEASQDM GRTLEWRPRT PALVRGCHLE GVAGHKEAHI LRVLPGHSAG PRTVTVKVEL   240
SCAPGDLDAV LILQGPPYVS WLIDANHNMQ IWTTGEYSFK IPPEKNIRGF KLPDTPQGLL   300
GEARMLNASI VASFVELPLA SIVSLHASSC GGRLQTSPAP IQTTPPKDTC SPELLMSLIQ   360
TKCADDAMTL VLKKELVAHL KCTITGLTFW DPSCEAEDRG DKFVLRSAYS SCGMQVSASM   420
ISNEAVVNIL SSSSPQRKKV HCLNMDSLSF QLGLYLSPHF LQASNTIEPG QQSFVQVRVS   480
PSVSEFLLQL DSCHLDLGPE GGTVELIQGR AAKGNCVSLL SPSPEGDPRF SFLLHFYTVP   540
IPKTGTLSCT VALRPKTGSQ DQEVHRTVFM RLNIISPDLS GCTSKGLVLP AVLGITGFAF   600
LIGALLTTAAL WYIYSHTRSP SKREPVVAVA APASSESSST NHSIGSTQST PCSTSSMA    658

SEQ ID NO: 5             moltype = AA  length = 117
FEATURE                  Location/Qualifiers
source                   1..117
                         mol_type = protein
```

```
                                    organism = Homo sapiens
SEQUENCE: 5
MGAPTLPPAW  QPFLKDHRIS  TFKNWPFLEG  CACTPERMAE  AGFIHCPTEN  EPDLAQWVFC     60
FKELEGWEPD  DDPIEEHKKH  SSGCAFLSVK  KQFEELTLGE  FLKLVRETLP  PPRSFIR       117

SEQ ID NO: 6              moltype = AA   length = 652
FEATURE                   Location/Qualifiers
source                    1..652
                          mol_type = protein
                          organism = Homo sapiens
SEQUENCE: 6
MATSMGLLLL  LLLLLTQPGA  GTGADTEAVV  CVGTACYTAH  SGKLSAAEAQ  NHCNQNGGNL     60
ATVKSKEEAQ  HVQRVLAQLL  RREAALTARM  SKFWIGLQRE  KGKCLDPSLP  LKGFSWVGGG    120
EDTPYSNWHK  ELRNSCISKR  CVSLLLDLSQ  PLLPSRLPKW  SEGPCGSPGS  PGSNIEGFVC    180
KFSFKGMCRP  LALGGPGQVT  YTTPFQTTSS  SLEAVPFASA  ANVACGEGDK  DETQSHYFLC    240
KEKAPDVFDW  GSSGPLCVSP  KYGCNFNNGG  CHQDCFEGGD  GSFLCGCRPG  FRLLDDLVTC    300
ASRNPCSSSP  CRGGATCVLG  PHGKNYTCRC  PQGYQLDSSQ  LDCVDVDECQ  DSPCAQEVCN    360
TPGGFRCECW  VGYEPGGPGE  GACQDVDECA  LGRSPCAQGC  TNTDGSFHCS  CEEGYVLAGE    420
DGTQCQDVDE  CVGPGGPLCD  SLCFNTQGSF  HCGCLPGWVL  APNGVSCTMG  PVSLGPPSGP    480
PDEEDKGEKE  GSTVPRAATA  SPTRGPEGTP  KATPTTSRPS  LSSDAPITSA  PLKMLAPSGS    540
SGVWREPSIH  HATAASGPQE  PAGGDSSVAT  QNNDGTDGQK  LLLFYILGTV  VAILLLLALA    600
LGLLVYRKRR  AKREEKKEKK  PQNAADSYSW  VPERAESRAM  ENQYSPTPGT  DC            652

SEQ ID NO: 7              moltype = AA   length = 277
FEATURE                   Location/Qualifiers
source                    1..277
                          mol_type = protein
                          organism = Homo sapiens
SEQUENCE: 7
MWPGILVGGA  RVASCRYPAL  GPRLAAHFPA  QRPPQRTLQN  GLALQRCLHA  TATRALPLIP     60
IVVEQTGRGE  RAYDIYSRLL  RERIVCVMGP  IDDSVASLVI  AQLLFLQSES  NKKPIHMYIN    120
SPGGVVTAGL  AIYDTMQYIL  NPICTWCVGQ  AASMGSLLLA  AGTPGMRHSL  PNSRIMIHQP    180
SGGARGQATD  IAIQAEEIMK  LKKQLYNIYA  KHTKQSLQVI  ESAMERDRYM  SPMEAQEFGI    240
LDKVLVHPPQ  DGEDEPTLVQ  KEPVEAAPAA  EPVPAST                              277

SEQ ID NO: 8              moltype = AA   length = 285
FEATURE                   Location/Qualifiers
source                    1..285
                          mol_type = protein
                          organism = Homo sapiens
SEQUENCE: 8
MAAAEAANCI  MEVSCGQAES  SEKPNAEDMT  SKDYYFDSYA  HFGIHEEMLK  DEVRTLTYRN     60
SMFHNRHLFK  DKVVLDVGSG  TGILCMFAAK  AGARKVIGIE  CSSISDYAVK  IVKANKLDHV    120
VTIIKGKVEE  VELPVEKVDI  IISEWMGYCL  FYESMLNTVL  YARDKWLEVD  IYTVKVEDLT    180
FTSPFCLQVK  RNDYVHALVA  YFNIEFTRCH  KRTGFSTSPE  SPYTHWKQTV  FYMEDYLTVK    240
TGEEIFGTIG  MRPNAKNNRD  LDFTIDLDFK  GQLCELSCST  DYRMR                    285

SEQ ID NO: 9              moltype = AA   length = 609
FEATURE                   Location/Qualifiers
source                    1..609
                          mol_type = protein
                          organism = Homo sapiens
SEQUENCE: 9
MKWVESIFLI  FLLNFTESRT  LHRNEYGIAS  ILDSYQCTAE  ISLADLATIF  FAQFVQEATY     60
KEVSKMVKDA  LTAIEKPTGD  EQSSGCLENQ  LPAFLEELCH  EKEILEKYGH  SDCCSQSEEG    120
RHNCFLAHKK  PTPASIPLFQ  VPEPVTSCEA  YEEDRETFMN  KFIYEIARRH  PFLYAPTILL    180
WAARYDKIIP  SCCKAENAVE  CFQTKAATVT  KELRESSLLN  QHACAVMKNF  GTRTFQAITV    240
TKLSQKFTKV  NFTEIQKLVL  DVAHVHEHCC  RGDVLDCLQD  GEKIMSYICS  QQDTLSNKIT    300
ECCKLTTLER  GQCIIHAEND  EKPEGLSPNL  NRFLGDRDFN  QFSSGEKNIF  LASFVHEYSR    360
RHPQLAVSVI  LRVAKGYQEL  LEKCFQTENP  LECQDKGEEE  LQKYIQESQA  LAKRSCGLFQ    420
KLGEYYLQNA  FLVAYTKKAP  QLTSSELMAI  TRKMAATAAT  CCQLSEDKLL  ACGEGAADII    480
IGHLCIRHEM  TPVNPGVGQC  CTSSYANRRP  CFSSLVVDET  YVPPAFSDDK  FIFHKDLCQA    540
QGVALQTMKQ  EFLINLVKQK  PQITEEQLEA  VIADFSGLLE  KCCQGQEQEV  CFAEEGQKLI    600
SKTRAALGV                                                                609

SEQ ID NO: 10             moltype = AA   length = 43
FEATURE                   Location/Qualifiers
source                    1..43
                          mol_type = protein
                          organism = Homo sapiens
SEQUENCE: 10
MAARAVFLAL  SAQLLQARLM  KEESPVVSWR  LEPEDGTALC  FIF                       43

SEQ ID NO: 11             moltype = AA   length = 198
FEATURE                   Location/Qualifiers
source                    1..198
                          mol_type = protein
                          organism = Homo sapiens
SEQUENCE: 11
```

```
LVSEVIRFIL FKFHQSSGTP IKREDLTQIV TKNYRQRNLA THVINEAKKK LSNVFGYDLK    60
ELQRARASST GQSRLPQSQS SVDSKSYVLV SELPLEVFKK HVVDETTSPV TGFTFVVLAI   120
VQLAGGKIPE ETLWHHLKRM GLHENDEHNP VFGNNKQTLE TLVQQRFLQK EKVSGPEGST   180
LVYDLAERAL DPQVSEKV                                                 198

SEQ ID NO: 12           moltype = AA   length = 562
FEATURE                 Location/Qualifiers
source                  1..562
                        mol_type = protein
                        organism = Homo sapiens
SEQUENCE: 12
MSNQYQEEGC SERPECKSKS PTLLSSYCID SILGRRSPCK MRLLGAAQSL PAPLTSRADP    60
EKAVQGSPKS SSAPFEAELH LPPKLRRLYG PGGGRLLQGA AAAAAAAAA AAAAATATAG   120
PRGEAPPPPP PTARPGERPD GAGAAAAAAA AAAAAWDTLK ISQAPQVSIS RSKSYRENGA   180
PFVPPPPALD ELGGPGGVTH PEERLGVAGG PGSAPAAGGG TGTEDDEEEL LEDEEDEDEE   240
EELLEDDEEE LLEDDARALL KEPRRCPVAA TGAVAAAAAA AVATEGGELS PKEELLLHPE   300
DAEGKDGEDS VCLSAGSDSE EGLLKRKQRR YRTTFTSYQL EELERAFQKT HYPDVFTREE   360
LAMRLDLTEA RVQVWFQNRR AKWRKREKAG AQTHPPGLPF PGPLSATHPL SPYLDASPFP   420
PHHPALDSAW TAAAAAAAAA FPSLPPPPGS ASLPPSGAPL GLSTFLGAAV FRHPAFISPA   480
FGRLFSTMAP LTSASTAAAL LRQPTPAVEG AVASGALADP ATAAADRRAS SIAALRLKAK   540
EHAAQLTQLN ILPGTSTGKE VC                                            562

SEQ ID NO: 13           moltype = AA   length = 501
FEATURE                 Location/Qualifiers
source                  1..501
                        mol_type = protein
                        organism = Homo sapiens
SEQUENCE: 13
MAPDKFLSTI TAGLMNFTGA DIPPLSTRDQ YATVNHHVHE ARMENGQRKQ DNVLSNVLSG    60
LINMAGASIP AMSSRDLYAT ITHSVREEKM ESGKPQTDKV ISNDAPQLGH MAAGGIPSMS   120
TKDLYATVTQ NVHEERMENN QPQPSYDLST VLPGLTYLTV AGIPAMSTRD QYATVTHNVH   180
EEKIKNGQAA SDNVFSTVPP AFINMAATGV SSMSTRDQYA AVTHNIREEK INNSQPAPGN   240
ILSTAPPWLR HMAAAGISST ITRDLYVTAT HSVHEEKMTN GQQAPDNSLS TVPPGCINLS   300
GAGISCRSTR DLYATVIHDI QEEEMENDQT PPDGFLSNSD SPELINMTGH CMPPNALDSF   360
SHDFTSLSKD ELLYKPDSNE FAVGTKNYSV SAGDPPVTVM SLVETVPNTP QISPAMAKKI   420
NDDIKYQLMK EVRRFGQNYE RIFILLEEVQ GSMKVKRQFV EFTIKEAARF KKVVLIQQLE   480
KALKEIDSHC HLRKVKHMRK R                                             501

SEQ ID NO: 14           moltype = AA   length = 636
FEATURE                 Location/Qualifiers
source                  1..636
                        mol_type = protein
                        organism = Homo sapiens
SEQUENCE: 14
MSFLIKGAQK HGFICQTHKE LFKRCILKSS KTFNGQKMIS SQASSPVNSK NMDSFNYIIV    60
GAGSAGCVLA NRLTENPHNT VKLLEAGPKD TVLGSKQLSW KIHMPAALTY NLCDEKYNWY   120
YHTTPQKHMD NRILYWPRGR VWGGSSSLNA MVYIRGHAED YNRWSKEGAV GWDYEFCLPY   180
FKKAQTHELG ADLYRGGDGP LHVSRGKTKN PLHCAFLDAA QQAGYPFTDD MNGFQQEGFG   240
WMDMTIYEDF PRAVYHTEIS YIICIGYCYN KNVYFVGKRW NTASAYLRPA LSRPNLSAEV   300
STLVTKVLFE GTKAIGIEYI KNGEKKKVFA SKEVILSGGA INSPQLLMLS GVGVGQNLQD   360
HLEVYIQQKC TQPLTLYKSQ KPLQMIKIGL EWFWKSTGDG ATAHLETGGF IRSRPGISHP   420
DIQFHFLPSQ VIDHGRVASQ LEAYQVHIGP MRSTSVGKLK LKSSDPTEHP ILEPNYLSTE   480
MDVWEFRQCV KLAREIFAQK AFEEFRGPEI QPGEHIQSDK EIDAFIRQKS DSAYHPSCTC   540
KMGQNSDPMA VVNPETKVIG TENLRVVDAS IMPSIVSGNL NAPTIMIAEK AADIILGLPP   600
LQEKNVPVYK PKTLETQHNP DKVAWQNKSI YPMLIK                             636

SEQ ID NO: 15           moltype = AA   length = 140
FEATURE                 Location/Qualifiers
source                  1..140
                        mol_type = protein
                        organism = Homo sapiens
SEQUENCE: 15
LLYKPVDRVT RSTLVLHDLL KHTPASHPDH PLLQDALRIS QNFLSSINEE ITPRRQSMTV    60
KKGEGEDRMK ASSTRKRLLL MEEALQRPVA SDFEPQGLSE AARWNSKENL LAGPSENDPN   120
LFVALYDFVA SGDNTLSITK                                               140

SEQ ID NO: 16           moltype = AA   length = 109
FEATURE                 Location/Qualifiers
source                  1..109
                        mol_type = protein
                        organism = Homo sapiens
SEQUENCE: 16
MLMAQEALAF LMAQGAMLAA QERRVPRAAE VPGAQGQQGP RGREEAPRGV RMAVPLLRRM    60
EGAPAGPGGR TAACFSCTSR CLSRRPWKRS WSAGSCPGMP HLSPDQGRF               109

SEQ ID NO: 17           moltype = AA   length = 222
FEATURE                 Location/Qualifiers
source                  1..222
                        mol_type = protein
```

```
                        organism  = Homo sapiens
SEQUENCE: 17
MFSLSTVAFL  VLLSTSGHAS  MCPDNNGMSD  EVRNTFLKKH  NAYRTLVAKG  EAKNAKEIGG   60
YAPKAARMLK  VTYDCAIEEN  TMNFAKKCVF  AHNSYKDRNY  WGQNFYMTSI  LNQNKTAAA   120
ESVDLWFDEL  QQNGVPVDNV  MTMAVFNRGV  GHYTQVVWQW  SNKIGCAVEW  CSDMTFVACE  180
YDSAGNYMGM  PIYEVGNPCT  NNEDCKCTNC  VCSREEALCI  AP                      222

SEQ ID NO: 18           moltype = AA  length = 702
FEATURE                 Location/Qualifiers
source                  1..702
                        mol_type = protein
                        organism = Homo sapiens
SEQUENCE: 18
MESPSAPPHR  WCIPWQRLLL  TASLLTFWNP  PTTAKLTIES  TPFNVAEGKE  VLLLVHNLPQ   60
HLFGYSWYKG  ERVDGNRQII  GYVIGTQQAT  PGPAYSGREI  IYPNASLLIQ  NIIQNDTGFY  120
TLHVIKSDLV  NEEATGQFRV  YPELPKPSIS  SNNSKPVEDK  DAVAFTCEPE  TQDATYLWVV  180
NNQSLPVSPR  LQLSNGNRTL  TLFNVTRNDT  ASYKCETQNP  VSARRSDSVI  LNVLYGPDAP  240
TISPLNTSYR  SGENLNLSCH  AASNPPAQYS  WFVNGTFQQS  TQELFIPNIT  VNNSGSYTCQ  300
AHNSDTGLNR  TTVTTITVYA  EPPKPFITSN  NSNPVEDEDA  VALTCEPEIQ  NTTYLWWVNN  360
QSLPVSPRLQ  LSNDNRTLTL  LSVTRNDVGP  YECGIQNELS  VDHSDPVILN  VLYGPDDPTI  420
SPSYTYYRPG  VNLSLSCHAA  SNPPAQYSWL  IDGNIQQHTQ  ELFISNITEK  NSGLYTCQAN  480
NSASGHSRTT  VKTITVSAEL  PKPSISSNNS  KPVEDKDAVA  FTCEPEAQNT  TYLWWVNGQS  540
LPVSPRLQLS  NGNRTLTLFN  VTRNDARAYV  CGIQNSVSAN  RSDPVTLDVL  YGPDTPIISP  600
PDSSYLSGAN  LNLSCHSASN  PSPQYSWRIN  GIPQQHTQVL  FIAKITPNNN  GTYACFVSNL  660
ATGRNNSIVK  SITVSASGTS  PGLSAGATVG  IMIGVLVGVA  LI                      702

SEQ ID NO: 19           moltype = AA  length = 278
FEATURE                 Location/Qualifiers
source                  1..278
                        mol_type = protein
                        organism = Homo sapiens
SEQUENCE: 19
MDFSRNLYDI  GEQLDSEDLA  SLKFLSLDYI  PQRKQEPIKD  ALMLFQRLQE  KRMLEESNLS   60
FLKELLFRIN  RLDLLITYLN  TRKEEMEREL  QTPGRAQISA  YRVMLYQISE  EVSRSELRSF  120
KFLLQEEISK  CKLDDDMNLL  DIFIEMEKRV  ILGEGKLDIL  KRVCAQINKS  LLKIINDYEE  180
FSKGEELCGV  MTISDSPREQ  DSESQTLDKV  YQMKSKPRGY  CLIINNHNFA  KAREKVPKLH  240
SIRDRNGTHL  DAGSHSVAQA  GVQWCDLGSL  QPPPPPWFG                           278

SEQ ID NO: 20           moltype = AA  length = 303
FEATURE                 Location/Qualifiers
source                  1..303
                        mol_type = protein
                        organism = Homo sapiens
SEQUENCE: 20
MATSRYEPVA  EIGVGAYGTV  YKARDPHSGH  FVALKSVRVP  NGGGGGGGLP  INTVREVALL   60
RRLEAFEHPN  VVRLMDVCAT  SRTDREIKVT  LVFEHVDQDL  RTYLDKAPPP  GLPAETIKDL  120
MRQFLRGLDF  LHANCIVHRD  LKPENILVTS  GGTVKLADFG  LARIYSYQMA  LTPVVVTLWY  180
RAPEVLLQST  YATPVDMWSV  GCIFAEMFRR  KPLFCGNSEA  DQLGKIFDLI  GLPPEDDWPR  240
DVSLPRGAFP  PRGPRPVQSV  VPEMEESGAQ  LLLEMLTFNP  HKRISAFRAL  QHSYLHKDEG  300
NPE                                                                     303

SEQ ID NO: 21           moltype = AA  length = 823
FEATURE                 Location/Qualifiers
source                  1..823
                        mol_type = protein
                        organism = Homo sapiens
SEQUENCE: 21
MTVLQEPVQA  AIWQALNHYA  YRDAVFLAER  LYAEVHSEEA  LFLLATCYYR  SGKAYKAYRL   60
LKGHSCTTPQ  CKYLLAKCCV  DLSKLAEGEQ  ILSGGVFNKQ  KSHDDIVTEF  GDSACFTLSL  120
LGHVYCKTDR  LAKGSECYQK  SLSLNPFLWS  PFESLCEIGE  KPDPDQTFKF  TSLQNFSNCL  180
PNSCTTQVPN  HSLSHRQPET  VLTETPQDTI  ELNRLNLESS  NSKYSLNTDS  SVSYIDSAVI  240
SPDTVPLGTG  TSILSKQVQN  KPKTGRSLLG  GPAALSPLTP  SFGILPLETP  SPGDGSYLQN  300
YTNTPPVIDV  PSTGAPSKKS  VARIGQTGTK  SVFSQSGNSR  EVTPILAQTQ  SSGPQTSTTP  360
QVLSPTITSP  PNALPRRSSR  LFTSDSSTTK  ENSKKLKMKF  PPKIPNRKTK  SKTNKGGITQ  420
PNINDSLEIT  KLDSSIISEG  KISTITPQIQ  AFNLQKAAAG  LMSLLREMGK  GYLALCSYNC  480
KEAINILSHL  PSHHYNTGWV  LCQIGRAYFE  LSEYMQAERI  FSEVRRIENY  RVEGMEIYST  540
TLWHLQKDVA  LSVLSKDLTD  MDKNSPEAWC  AAGNCFSLQR  EHDIAIKFFQ  RAIQVDPNYA  600
YAYTLLGHEF  VLTEELDKAL  ACFRNAIRVN  PRHYNAWYGL  GMIYYKQEKF  SLAEMHFQKA  660
LDINPQSSVL  LCHIGVVQHA  LKKSEKALDT  LNKAIVIDPK  NPLCKFHRAS  VLFRNEKYKS  720
ALQELEELKQ  IVPKESLVYF  LIGKVYKKLG  QTHLALMNFS  WAMDLDPKGA  NNQIKEAIDK  780
RYLPDDEEPI  TQEEQIMGTD  ESQESSMTDA  DDTQLHAAES  DEF                     823

SEQ ID NO: 22           moltype = AA  length = 382
FEATURE                 Location/Qualifiers
source                  1..382
                        mol_type = protein
                        organism = Homo sapiens
SEQUENCE: 22
MGLLLPLALC  ILVLCCGAMS  PPQLALNPSA  LLSRGCNDSD  VLAVAGFALR  DINKDRKDGY   60
```

```
VLRLNRVNDA QEYRRGGLGS LFYLTLDVLE TDCHVLRKKA WQDCGMRIFF ESVYGQCKAI    120
FYMNNPSRVL YLAAYNCTLR PVSKKKIYMT CPDCPSSIPT DSSNHQVLEA ATESLAKYNN    180
ENTSKQYSLF KVTRASSQWV VGPSYFVEYL IKESPCTKSQ ASSCSLQSSD SVPVGLCKGS    240
LTRTHWEKFV SVTCDFFESQ APATGSENSA VNQKPTNLPK VEESQQKNTP PTDSPSKAGP    300
RGPVQYLPDL DDKNSQEKGP QEAFPVHLDL TTNPQGETLD ISFLFLEPME EKLVVLPFPK    360
EKARTAECPG PAQNASPLVL PP                                            382

SEQ ID NO: 23           moltype = AA  length = 257
FEATURE                 Location/Qualifiers
source                  1..257
                        mol_type = protein
                        organism = Homo sapiens
SEQUENCE: 23
MPFISHHYPH DHSCRWVEPF IGGGAVFLNM FAQNALLADS NPDLINLYRT IQRQKTNFIN     60
QVQNLADKTF VEKDYYEMRD RFNKTCISGQ PLQRAALFYS LNRLGYNGMC RYNSERIYSV    120
PWGKHTELKL DFNKIDYLSF RLSGIELITA GFEETLAATG EGDQIYCDPP YDKTSKTSFV    180
SYDGKPFSQS DHVLLANMLV DAHRKGAAVA ISNSLTPFTL GLYEERGFVI HRLSAYRSVG    240
SKPNTRKTET EILAVLK                                                  257

SEQ ID NO: 24           moltype = AA  length = 288
FEATURE                 Location/Qualifiers
source                  1..288
                        mol_type = protein
                        organism = Homo sapiens
SEQUENCE: 24
MNAKKNPLVK PFLKWAGGKR QLLPEILKYL PKNIGKTTYF EPFLGGGALL FELQPKQAIV     60
NDSNRELINC YRVIKDNVEE LIEVLKHVKA KNSKEYFDYL RERDRLKQYN KFSDIQKAAR    120
IIYLNKTCYN GLFRVNSKGQ FNVPFGSYKN PNILDEAVLR GVNDYLNQKS VTFLNIDFAE    180
AVKDAKKGDF VYFDPPYDPV SNTASFTGYD INGFNQNEQR RLKQVVDELT EKGCNVMLSN    240
SATDFILDLY KDHKYTIETV SATRSINSNA LKRGKINEVL VLNYVPKL                288

SEQ ID NO: 25           moltype = AA  length = 395
FEATURE                 Location/Qualifiers
source                  1..395
                        mol_type = protein
                        organism = Homo sapiens
SEQUENCE: 25
GPGCNTKKPN LDAELDQLLQ GHYIKGYPKQ YTYFLEDGKV KVSRPEGVKI IPPQSDRQKI     60
VLQAHNLAHT GREATLLKIA NLYWWPNMRK DVVKQLGRCQ QCLITNASNK ASGPILRPDR    120
PQKPFDKFFI DYIGPLPPSQ GYLYVLVVVD GMTGFTWLYP TKAPSTSATV KSLNVLTSIA    180
IPKVIHSDQG AAFTSSTFAE WAKERGIHLE FSTPYHPQSS GKVERKNSDI KRLLTKLLVG    240
RPTKWYDLLP VVQLALNNTY SPVLKYTPHQ LLFGIDSNTP FANQDTLDLT REEELSLLQE    300
IRTSLYHPST PPASSRSWSP VVGQLVQERV ARPASLRPRW HKPSTVLKVL NPRTVVILDH    360
LGNNRTVSID NLKPTSHQNG TTNDTATMDH LEKNE                              395

SEQ ID NO: 26           moltype = AA  length = 395
FEATURE                 Location/Qualifiers
source                  1..395
                        mol_type = protein
                        organism = Homo sapiens
SEQUENCE: 26
GPGCNTKKPN LDAELDQLLQ GHYIKGYPKQ YTYFLEDGKV KVSRPEGVKI IPPQSDRQKI     60
VLQAHNLAHT GREATLLKIA NLYWWPNMRK DVVKQLGRCQ QCLITNASNK ASGPILRPDR    120
PQKPFDKFFI DYIGPLPPSQ GYLYVLVVVD GMTGFTWLYP TKAPSTSATV KSLNVLTSIA    180
IPKVIHSDQG AAFTSSTFAE WAKERGIHLE FSTPYHPQSS GKVERKNSDI KRLLTKLLVG    240
RPTKWYDLLP VVQLALNNTY SPVLKYTPHQ LLFGIDSNTP FANQDTLDLT REEELSLLQE    300
IRTSLYHPST PPASSRSWSP VVGQLVQERV ARPASLRPRW HKPSTVLKVL NPRTVVILDH    360
LGNNRTVSID NLKPTSHQNG TTNDTATMDH LEKNE                              395

SEQ ID NO: 27           moltype = AA  length = 407
FEATURE                 Location/Qualifiers
source                  1..407
                        mol_type = protein
                        organism = Homo sapiens
SEQUENCE: 27
MGVLTKSLQK ESAKTNKRDD YSAADLMHVP TGFDAIDYEG GTIVEDIDGD PMLNIGLPMG     60
KIILCCGNSQ AGKTTGALQF ANGMASHLDG DVVIFDFERG ILDPRSRIRN LCRLSNDEYD    120
NRFTIYKNAG MSVEFFKKQI FKIVELKEKL AKADMVDWYM LNGAPVKIYP PTYVLLDSIP    180
SMKPEDVLND SSLDNNMVFS KMAAANSAML TSIVNVLEKY NITLICINHI TTKIIINAYG    240
PRKVLLPGME PEENLPGGNK FVYLPSYVLK FASGKALNKD KDFKVNGRVT NCTFLKSRSS    300
FNGAKLPLAV TEKHGFSNVM TNILAMKEEK MLKGTGQGGF WFEGHEDMKF KQSEFIKKYN    360
KDTEFQEMFD EVSSEFWQGR LEDRFGDEYD SVEKSKGNDF DDDDDDE                 407

SEQ ID NO: 28           moltype = AA  length = 661
FEATURE                 Location/Qualifiers
source                  1..661
                        mol_type = protein
                        organism = Homo sapiens
SEQUENCE: 28
```

```
MDLVLKRCLL HLAVIGALLA VGATKVPRNQ DWLGVSRQLR TKAWNRQLYP EWTEAQRLDC    60
WRGGQVSLKV SNDGPTLIGA NASFSIALNF PGSQKVLPDG QVIWVNNTII NGSQVWGGQP   120
VYPQETDDAC IFPDGGPCPS GSWSQKRSFV YVWKTWGQYW QVLGGPVSGL SIGTGRAMLG   180
THTMEVTVYH RRGSRSYVPL AHSSSAFTIT DQVPFSVSVS QLRALDGGNK HFLRNQPLTF   240
ALQLHDPSGY LAEADLSYTW DFGDSSGTLI SRALVVTHTY LEPGPVTAQV VLQAAIPLTS   300
CGSSPVPGTT DGHRPTAEAP NTTAGQVPTT EVVGTTPGQA PTAEPSGTTS VQVPTTEVIS   360
TAPVQMPTAE STGMTPEKVP VSEVMGTTLA EMSTPEATGM TPAEVSIVVL SGTTAAQVTT   420
TEWVETTARE LPIPEPEGPD ASSIMSTESI TGSLGPLLDG TATLRLVKRQ VPLDCVLYRY   480
GSFSVTLDIV QGIESAEILQ AVPSGEGDAF ELTVSCQGGL PKEACMEISS PGCQPPAQRL   540
CQPVLPSPAC QLVLHQILKG GSGTYCLNVS LADTNSLAVV STQLIMPGQE AGLGQVPLIV   600
GILLVLMAVV LASLIYRRRL MKQDFSVPQL PHSSSHWLRL PRIFCSCPIG ENSPLLSGQQ   660
V                                                                  661

SEQ ID NO: 29         moltype = AA  length = 648
FEATURE               Location/Qualifiers
source                1..648
                      mol_type = protein
                      organism = Homo sapiens
SEQUENCE: 29
MSHHGGAPKA STWVVASRRS STVSRAPERR PAEELNRTGP EGYSVGRGGR WRGTSRPPEA    60
VAAGHEELPL CFALKSHFVG AVIGRGGSKI KNIQSTTNTT IQIIQEQPES LVKIFGSKAM   120
QTKAKAVIDN FVKKLEENYN SECGIDTAFQ PSVGKDGSTD NNVVAGDRPL IDWDQIREEG   180
LKWQKTKWAD LPPIKKNFYK ESTATSAMSK VEADSWRKEN FNITWDDLKD GEKRPIPNPT   240
CTFDDAFQCY PEVMENIKKA GFQKPTPIQS QAWPIVLQGI DLIGVAQTGT GKTLCYLMPG   300
FIHLVLQPSL KGQRNRPGML VLTPTRELAL QVEGECCKYS YKGLRSVCVY GGGNRDEQIE   360
ELKKGVDIII ATPGRLNDLQ MSNFVNLKNI TYLVLDEADK MLDMGFEPQI MKILLDVRPD   420
RQTVMTSATW PHSVHRLAQS YLKEPMIVYV GTLDLVAVSS VKQNIIVTTE EEKWSHMQTF   480
LQSMSSTDKV IVFVSRKAVA DHLSSDLILG NISVESLHGD REQRDREKAL ENFKTGKVRI   540
LIATDLASRG LDVHDVTHVY NFDFPRNIEE YVHRIGRTGR AGRTGVSITT LTRNDWRVAS   600
ELINILERAN QSIPEELVSM AERFKAHQQK REMERKMERP QGRPKKFH                648

SEQ ID NO: 30         moltype = AA  length = 1240
FEATURE               Location/Qualifiers
source                1..1240
                      mol_type = protein
                      organism = Homo sapiens
SEQUENCE: 30
MPRGSWKPQV CTGTDMKLRL PASPETHLDM LRHLYQGCQV VQGNLELTYL PTNASLSFLQ    60
DIQEVQGYVL IAHNQVRQVP LQRLRIVRGT QLFEDNYALA VLDNGDPLNN TTPVTGASPG   120
GLRELQLRSL TEILKGGVLI QRNPQLCYQD TILWKDIFHK NNQLALTLID TNRSRACHPC   180
SPMCKGSRCW GESSEDCQSL TRTVCAGGCA RCKGPLPTDC CHEQCAAGCT GPKHSDCLAC   240
LHFNHSGICE LHCPALVTYN TDTFESMPNP EGRYTFGASC VTACPYNYLS TDVGSCTLVC   300
PLHNQEVTAE DGTQRCEKCS KPCARVCYGL GMEHLREVRA VTSANIQEFA GCKKIFGSLA   360
FLPESFDGDP ASNTAPLQPE QLQVFETLEE ITGYLYISAW PDSLPDLSVF QNLQVIRGRI   420
LHNGAYSLTL QGLGISWLGL RSLRELGSGL ALIHHNTHLC FVHTVPWDQL FRNPHQALLH   480
TANRPEDECV GEGLACHQLC ARGHCWGPGP TQCVNCSQFL RGQECVEECR VLQGLPREYV   540
NARHCLPCHP ECQPQNGSVT CFGPEADQCV ACAHYKDPF CVARCPSGVK PDLSYMPIWK   600
FPDEEGACQP CPINCTHSCV DLDDDKGCPA EQRASPLTSII SAVVGILLVV VLGVVFGILI   660
KRRQQKIRKY TMRRLLQETE LVEPLTPSGA MPNQAQMRIL KETELRKVKV LGSGAFGTVY   720
KGIWIPDGEN VKIPVAIKVL RENTSPKANK EILDEAYVMA GVGSPYVSRL LGICLTSTVQ   780
LVTQLMPYGC LLDHVRENRG RLGSQDLLNW CMQIAKGMSY LEDVRLVHRD LAARNVLVKS   840
PNHVKITDFG LARLLDIDET EYHADGGKVP IKWMALESIL RRRFTHQSDV WSYGVTVWEL   900
MTFGAKPYDG IPAREIPDLL EKGERLPQPP ICTIDVYMIM VKCWMIDSEC RPRFRELVSE   960
FSRMARDPQR FVVIQNEDLG PASPLDSTFY RSLLEDDDMG DLVDAEEYLV PQQGFFCPDP  1020
APGAGGMVHH RHRSSSTRSG GGDLTLGLEP SEEEAPRSPL APSEGAGSDV FDGDLGMGAA  1080
KGLQSLPTHD PSPLQRYSED PTVPLPSETD GYVAPLTCSP QPEYVNQPDV RPQPPSPREG  1140
PLPAARPAGA TLERPKTLSP GKNGVVKDVF AFGGAVENPE YLTPQGGAAP QPHPPPAFSP  1200
AFDNLYYWDQ DPPERGAPPS TFKGTPTAEN PEYLGLDVPV                        1240

SEQ ID NO: 31         moltype = AA  length = 44
FEATURE               Location/Qualifiers
source                1..44
                      mol_type = protein
                      organism = Homo sapiens
SEQUENCE: 31
MNHPGLFLFL GLTFAVQLLL LVFLLFFFLV WWDQFGCRCD GFIL                     44

SEQ ID NO: 32         moltype = AA  length = 580
FEATURE               Location/Qualifiers
source                1..580
                      mol_type = protein
                      organism = Homo sapiens
SEQUENCE: 32
MAGTVRTACL VVAMLLSLDF PGQAQPPPPP PDATCHQVRS FFQRLQPGLK WVPETPVPGS    60
DLQVCLPKGP TCCSRKMEEK YQLTARLNME QLLQSASMEL KFLIIQNAAV FQEAFEIVVR   120
HAKNYTNAMF KNNYPSLTPQ AFEFVGEFFT DVSLYILGSD INVDDMVNEL FDSLFPVIYT   180
QLMNPGLPDS ALDINECLRG ARRDKVFGN FPKLIMTQVS KSLQVTRIFL QALNLGIEVI   240
NTTDHLKFSK DCGRMLTRMW YCSYCQGLMM VKPCGGYCNV VMQGCMAGVV EIDKYWREYI   300
LSLEELVNGM YRIYDMENVL LGLFSTIHDS IQYVQKNAGK LTTTIGKLCA HSQQRQYRSA   360
```

```
YYPEDLFIDK KVLKVAHVEH EETLSSRRRE LIQKLKSFIS FYSALPGYIC SHSPVAENDT    420
LCWNGQELVE RYSQKAARNG MKNQFNLHEL KMKGPEPVVS QIIDLKHIN  QLLRTMSMPK    480
GRVLDKNLDE EGFESGDCGD DEDECIGGSG DGMIKVKNQL RFLAELAYDL DVDDAPGNSQ    540
QATPKDNEIS TFHNLGNVHS PLKLLTSMAI SVVCFFFLVH                          580

SEQ ID NO: 33            moltype = AA   length = 1069
FEATURE                  Location/Qualifiers
source                   1..1069
                         mol_type = protein
                         organism = Homo sapiens
SEQUENCE: 33
MPRAPRCRAV RSLLRSHYRE VLPLATFVRR LGPQGWRLVQ RGDPAAFRAL VAQCLVCVPW     60
DARPPPAAPS FRQVSCLKEL VARVLQRLCE RGAKNVLAFG FALLDGARGG PPEAFTTSVR    120
SYLPNTVTDA LRGSGAWGLL LRRVGDDVLV HLLARCALFV LVAPSCAYQV CGPPLYQLGA    180
ATQARPPPHA SGPRRRLGCE RAWNHSVREA GVPLGLPAPG ARRRGGSASR SLPLPKRPRR    240
GAAPEPERTP VGQGSWAHPG RTRGPSDRGF CVVSPARPAE EATSLEGALS GTRHSHPSVG    300
RQHHAGPPST SRPPRPWDTP CPPVYAETKH FLYSSGDKEQ LRPSFLLSSL RPSLTGARRL    360
VETIFLGSRP WMPGTPRRLP RLPQRYWQMR PLFLELLGNH AQCPYGVLLK THCPLRAAVT    420
PAAGVCAREK PQGSVAAPEE EDTDPRRLVQ LLRRQHSSPWQ VYGFVRACLR RLVPPGLWGS    480
RHNERRFLRN TKKFISLGKH AKLSLQELTW KMSVRDCAWL RRSPGVGCVP AAEHRLREEI    540
LAKFLHWLMS VYVVELLRSF FYVTETTFQK NRLFFYRKSV WSKLQSIGIR QHLKRVQLRE    600
LSEAEVRQHR EARPALLTSR LRFIPKPDGL RPIVNMDYVV GARTFRREKR AERLTSRVKA    660
LFSVLNYERA RRPGLLGASV LGLDDIHRAW RTFVLRVRAQ DPPPELYFVK VDVTGAYDTI    720
PQDRLTEVIA SIIKPQNTYC VRRYAVVQKA AHGHVRKAFK SHVSTLTDLQ PYMRQFVAHL    780
QETSPLRDAV VIEQSSSLNE ASSGLFDVFL RFMCHHAVRI RGKSYVQCQG IPQGSILSTL    840
LCSLCYGDME NKLFAGIRRD GLLLRLVDDF LLVTPHLTHA KTFLSYARTS IRASLTFNRG    900
FKAGRNMRRK LFGVLRLKCH SLFLDLQVNS LQTVCTNIYK ILLLQAYRFH ACVLQLPFHQ    960
QVWKNPTFFL RVISDTASLC YSILKAKNAG MSLGAKGAAG PLPSEAVQWL CHQAFLLKLT   1020
RHRVTYVPLL GSLRTAQTQL SRKLPGTTLT ALEAAANPAL PSDFKTILD             1069

SEQ ID NO: 34            moltype = AA   length = 404
FEATURE                  Location/Qualifiers
source                   1..404
                         mol_type = protein
                         organism = Homo sapiens
SEQUENCE: 34
MADKVLKEKR KLFIRSMGEG TINGLLDELL QTRVLNKEEM EKVKRENATV MDKTRALIDS     60
VIPKGAQACQ ICITYICEED SYLAGTLGLS ADQTSGNYLN VKPFVKINHE FPAPQAVQDN    120
PAMPTSSGSE GNVKLCSLEE AQRIWKQKSA EIYPIMDKSS RTRLALIICN EEFDSIPRRT    180
GAEVDITGMT MLLQNLGYSV DVKKNLTASD MTTELEAFAH RPEHKTSDST FLVFMSGHGI R  240
EGICGKKHSE QVPDILQLNA IFNMLNTKNC PSLKDKPKVI IIQACRGDSP GVVWFKDSVG    300
VSGNLSLPTT EEFEDDAIKK AHIEKDFIAF CSSTPDNVSW RHPTMGSVFI GRLIEHMQEY    360
ACSCDVEEIF RKVRFSFEQP DGRAQMPTTE RVTLTRCFYL FPGH                    404

SEQ ID NO: 35            moltype = AA   length = 118
FEATURE                  Location/Qualifiers
source                   1..118
                         mol_type = protein
                         organism = Homo sapiens
SEQUENCE: 35
MPREDAHFIY GYPKKGHGHS YTTAEEAAGI GILTVILGVL LLIGCWYCRR RNGYRALMDK     60
SLHVGTQCAL TRRCPQEGFD HRDSKVSLQE KNCEPVVPNA PPAYEKLSAE QSPPPYSP      118

SEQ ID NO: 36            moltype = AA   length = 1255
FEATURE                  Location/Qualifiers
source                   1..1255
                         mol_type = protein
                         organism = Homo sapiens
SEQUENCE: 36
MTPGTQSPFF LLLLLTVLTV VTGSGHASST PGGEKETSAT QRSSVPSSTE KNAVSMTSSV     60
LSSHSPGSGS STTQGQDVTL APATEPASGS AATWGQDVTS VPVTRPALGS TTPPAHDVTS    120
APDNKPAPGS TAPPAHGVTS APDTRPAPGS TAPPAHGVTS APDTRPAPGS TAPPAHGVTS    180
APDTRPAPGS TAPPAHGVTS APDTRPAPGS TAPPAHGVTS APDTRPAPGS TAPPAHGVTS    240
APDTRPAPGS TAPPAHGVTS APDTRPAPGS TAPPAHGVTS APDTRPAPGS TAPPAHGVTS    300
APDTRPAPGS TAPPAHGVTS APDTRPAPGS TAPPAHGVTS APDTRPAPGS TAPPAHGVTS    360
APDTRPAPGS TAPPAHGVTS APDTRPAPGS TAPPAHGVTS APDTRPAPGS TAPPAHGVTS    420
APDTRPAPGS TAPPAHGVTS APDTRPAPGS TAPPAHGVTS APDTRPAPGS TAPPAHGVTS    480
APDTRPAPGS TAPPAHGVTS APDTRPAPGS TAPPAHGVTS APDTRPAPGS TAPPAHGVTS    540
APDTRPAPGS TAPPAHGVTS APDTRPAPGS TAPPAHGVTS APDTRPAPGS TAPPAHGVTS    600
APDTRPAPGS TAPPAHGVTS APDTRPAPGS TAPPAHGVTS APDTRPAPGS TAPPAHGVTS    660
APDTRPAPGS TAPPAHGVTS APDTRPAPGS TAPPAHGVTS APDTRPAPGS TAPPAHGVTS    720
APDTRPAPGS TAPPAHGVTS APDTRPAPGS TAPPAHGVTS APDTRPAPGS TAPPAHGVTS    780
APDTRPAPGS TAPPAHGVTS APDTRPAPGS TAPPAHGVTS APDTRPAPGS TAPPAHGVTS    840
APDTRPAPGS TAPPAHGVTS APDTRPAPGS TAPPAHGVTS APDTRPAPGS TAPPAHGVTS    900
APDTRPAPGS TAPPAHGVTS APDTRPAPGS TAPPAHGVTS APDNRPALGS TAPPVHNVTS    960
ASGSASGSAS TLVHNGTSAR ATTTPASKST PFSIPSHHSD TPTTLASHST KTDASSTHHS   1020
SVPPLTSSNH STSPQLSTGV SFFFLSFHIS NLQFNSSLED PSTDYYQELQ RDISEMFLQI   1080
YKQGGFLGLS NIKFRPGSVV VQLTLAFREG TINVHDVETQ FNQYKTEAAS RYNLTISDVS   1140
VSDVPFPFSA QSGAGVPGWG IALLVLVCVL VALAIVYLIA LAVCQRRKN  YGQLDIFPAR   1200
```

```
DTYHPMSEYP TYHTHGRYVP PSSTDRSPYE KVSAGNGGSS LSYTNPAVAA TSANL        1255

SEQ ID NO: 37            moltype = AA   length = 317
FEATURE                  Location/Qualifiers
source                   1..317
                         mol_type = protein
                         organism = Homo sapiens
SEQUENCE: 37
MPALGSPRRL LGSLNCTPPA TLPLTLAPNR TGPQCLEVSI PDGLFLSLGL VSLVENVLVV    60
AAIAKNRNLH SPMYYFICCL AMSDLLVSVS NVLETAVMLL LEAGVLATRA AVVQQLDNVI   120
DVLICSSMVS SLCFLGAIAV DRYISIFYAL RYHSVVTLPR AWRIIAAIWV ASILTSVLSI   180
TYYNHTVVLL CLVGFFIAML ALMAVLYVHM LARACQHARG IARLQKRQRP IHQGFGLKGA   240
ATLTILLGVF FLCWGPFFLH LSLIVLCPQH PTCGCIFKNF NLFLALIICN AIVDPLIYAF   300
RSQELRKTLQ EVLQCSW                                                 317

SEQ ID NO: 38            moltype = AA   length = 683
FEATURE                  Location/Qualifiers
source                   1..683
                         mol_type = protein
                         organism = Homo sapiens
SEQUENCE: 38
MSSGTMKFNG YLRVRIGEAV GLQPTRWSLR HSLFKKGHQL LDPYLTVSVD QVRVGQTSTK    60
QKTNKPTYNE EFCANVTDGG HLELAVFHET PLGYDHFVAN CTLQFQELLR TTGASDTFEG   120
WVDLEPEGKV FVVITLTGSF TEATLQRDRI FKHFTRKRQR AMRRRVHQIN GHKFMATYLR   180
QPTYCSHCRE FIWGVFGKQG YQCQVCTCVV HKRCHHLIVT ACTCQNNINK VDSKIAEQRF   240
GINIPHKFSI HNYKVPTFCD HCGSLLWGIM RQGLQCKICK MNVHIRCQAN VAPNCGVNAV   300
ELAKTLAGMG LQPGNISPTS KLVSRSTLRR QGKESSKEGN GIGVNSSNRL GIDNFEFIRV   360
LGKGSFGKVM LARVKETGDL YAVKVLKKDV ILQDDDVECT MTEKRILSLA RNHPFLTQLF   420
CCFQTPDRLF FVMEFVNGGD LMFHIQKSRR FDEARARFYA AEIISALMFL HDKGIIYRDL   480
KLDNVLLDHE GHCKLADFGM CKEGICNGVT TATFCGTPDY IAPEILQEML YGPAVDWWAM   540
GVLLYEMLCG HAPFEAENED DLFEAILNDE VVYPTWLHED ATGILKSFMT KNPTMRLGSL   600
TQGGEHAILR HPFFKEIDWA QLNHRQIEPP FRPRIKSRED VSNFDPDFIK EEPVLTPIDE   660
GHLPMINQDE FRNFSYVSPE LQP                                          683

SEQ ID NO: 39            moltype = AA   length = 376
FEATURE                  Location/Qualifiers
source                   1..376
                         mol_type = protein
                         organism = Homo sapiens
SEQUENCE: 39
MMASYPEPED AAGALLAPET GRTVKEPEGP PPSPGKGGGG GGGTAPEKPD PAQKPPYSYV    60
ALIAMAIRES AEKRLTLSGI YQYIIAKFPF YEKNKKGWQN SIRHNLSLNE CFIKVPREGG   120
GERKGNYWTL DPACEDMFEK GNYRRRRRMK RPFRPPPAHF QPGKGLFGAG GAAGGCGVAG   180
AGADGYGYLA PPKYLQSGFL NNSWPLPQPP SPMPYASCQM AAAAAAAAAA AAAGPGSPG   240
AAAVVKGLAG PAASYGPYTR VQSMALPPGV VNSYNGLGGP PAAPPPPPHP HPHPAHHLH   300
AAAAPPPAPP HHGAAAPPPG QLSPASPATA APPAPAPTSA PGLQFACARQ PELAMMHCSY   360
WDHDSKTGAL HSRLDL                                                  376

SEQ ID NO: 40            moltype = RNA  length = 19
FEATURE                  Location/Qualifiers
source                   1..19
                         mol_type = other RNA
                         organism = synthetic construct
SEQUENCE: 40
ttataatgac tggatgttc                                                19

SEQ ID NO: 41            moltype = RNA  length = 19
FEATURE                  Location/Qualifiers
source                   1..19
                         mol_type = other RNA
                         organism = synthetic construct
SEQUENCE: 41
gtctggtgta tgaagggtt                                                19

SEQ ID NO: 42            moltype = RNA  length = 19
FEATURE                  Location/Qualifiers
source                   1..19
                         mol_type = other RNA
                         organism = synthetic construct
SEQUENCE: 42
ctcctatttt ggtttatgc                                                19

SEQ ID NO: 43            moltype = RNA  length = 19
FEATURE                  Location/Qualifiers
source                   1..19
                         mol_type = other RNA
                         organism = synthetic construct
```

```
SEQUENCE: 43
gcagcgtctt tcagtgctt                                                    19
```